United States Patent
Kowa et al.

[11] Patent Number: 6,157,448
[45] Date of Patent: Dec. 5, 2000

[54] BIREFRINGENCE MEASUREMENT OPTICAL SYSTEM AND HIGH SPATIAL RESOLUTION POLARIMETRIC APPARATUS

[75] Inventors: Hiroyuki Kowa, Hamura; Norihiro Umeda, Fuchu; Shinji Mochiduki, Shimizu, all of Japan

[73] Assignee: Uniopt Co., Ltd., Kosai, Japan

[21] Appl. No.: 09/414,841

[22] Filed: Oct. 8, 1999

[51] Int. Cl.[7] .................................................. G01J 4/00
[52] U.S. Cl. ........................... 356/365; 356/366; 356/367
[58] Field of Search ............................. 356/365, 366, 356/367, 368, 364

[56] References Cited

U.S. PATENT DOCUMENTS

| | | |
|---|---|---|
| 4,681,450 | 7/1987 | Azzam . |
| 4,904,863 | 2/1990 | McDearmon .......................... 356/351 |
| 5,726,744 | 3/1998 | Ferdinand et al. ........................ 356/32 |
| 5,864,403 | 1/1999 | Ajji et al. ................................ 356/365 |

FOREIGN PATENT DOCUMENTS 8-327498  12/1996  Japan .

Primary Examiner—Frank G. Font
Assistant Examiner—Roy M. Punnoose
Attorney, Agent, or Firm—Oblon, Spivak, McClelland, Maier & Neustadt, P.C.

[57] ABSTRACT

The object of the present invention is to measure the amount of birefringence of a target while enhancing spatial resolution. A birefringence measurement optical system is comprised of a Stabilized Transverse Zeeman Laser emitting laser beam in a predetermined polarization state toward a target, a halfwave plate (polarized light emission optical system), a linear polarizer (polarized light detection optical system) detecting information on the retardation, main axial direction and optical rotation angle of the target as a light signal which can be polarimetrically analyzed through the target, and a photo detector converting the light signal from the linear polarizer into an electric signal and detecting the electric signal. An optical fiber (light transmission path) taking out part of light fluxes of the light signal and optically transmitting the part of the light fluxes from the target toward the photo detector, is arranged between the photo detector and the target.

18 Claims, 22 Drawing Sheets

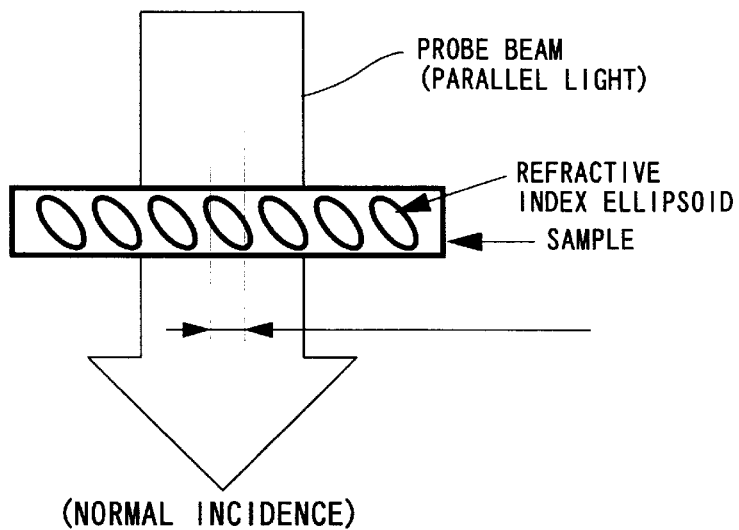
FIG. 32A
PRIOR ART
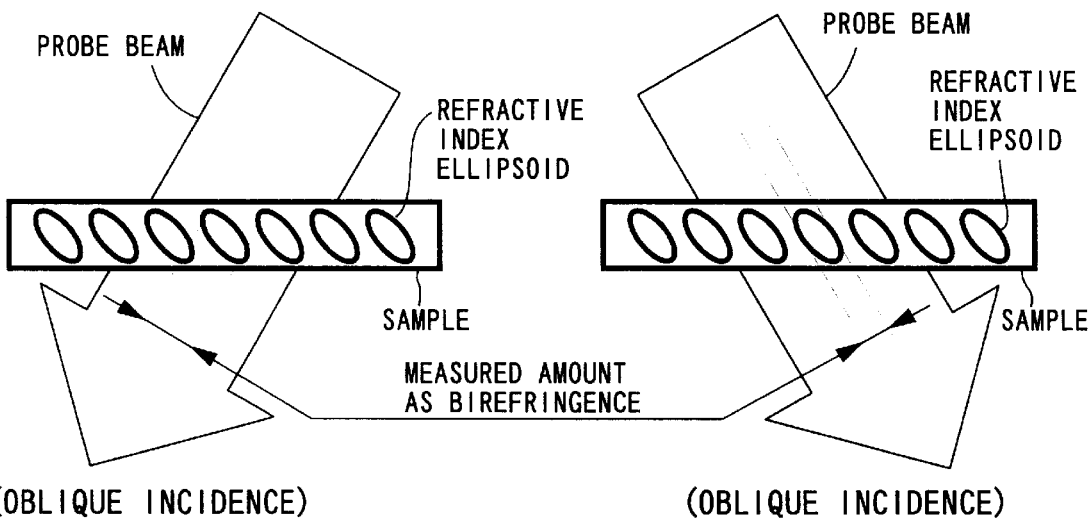
FIG. 32B
PRIOR ART
FIG. 32C
PRIOR ART

BIREFRINGENCE MEASUREMENT OPTICAL SYSTEM AND HIGH SPATIAL RESOLUTION POLARIMETRIC APPARATUS

BACKGROUND OF THE INVENTION

1. Field of the Invention

The present invention relates to a birefringence measurement optical system for measuring the birefringence of a sample such as a DVD (Digital Video Disc), a liquid crystal display and the like and relates to a high spatial resolution polarimetric apparatus. The present invention particularly relates to a device of an optical constitution which can be polarimetrically analyzed with high spatial resolution.

2. Description of the Related Art

In recent years, there is strong demand for a high-density recording medium and a high precision display device as a constituent technique in the field of rapidly developing multimedia. A DVD, for example, is intended to realize a high-density recorded signal by providing material with low birefringence and high qualilty. A liquid crystal display is intended to realize high precision by transferring SVGA (Super Video Gate Array) to XGA (Extended Graphics Array).

Among material evaluation techniques to obtain these objects, attention is attracted by, in particular, a quantitative birefringence measurement technique for measuring the state of birefringence in the vicinity of a signal pit for, for example, a DVD, birefringence information in pixel units for a liquid crystal display or the like on a microscopic scale.

As such birefringence measurement apparatuses, there have been conventionally known a polarizing microscope and a polarimetric apparatus. The polarizing microscope, however, employs an optical microscope incorporating a polarizer and a phase plate, with which microscope, the state of a birefringence distribution is observed qualitatively and intuitively with a magnification according to a combination of an objective lens and an eyepiece. The polarizing microscope is not, therefore, available for the quantitative measurement stated above.

The polarimetric apparatus adopts, for example, a method using a rotating analyzer, a phase compensation method, a Senarmont method, a phase modulation method, an optical heterodyne method or the like. Since this apparatus is designed to receive the overall light fluxes passing through the sample at the photo detector, the spatial resolution is determined by the size of diameter of the light fluxes and the positional resolution for measurement is limited to about 0.5 mm. For these reasons, it is difficult to use the apparatus for microscopic measurement as it is.

Considering the above disadvantages, as one of the approaches for quantitatively, microscopically measuring birefringence, a method of converging a light signal on a sample using a convergent lens which is added to the optical system of the above-stated polarimetric apparatus or the like is desired. In this method, a beam can be passed though an extremely limited region of the sample and it is, therefore, possible to further enhance spatial resolution.

In the polarimetric apparatus using the convergent lens as stated above, although spatial resolution on the sample enhances, light fluxes within a light beam have different incidence angles with respect to the sample. Due to this, the following disadvantages occur.

FIGS. 32A to 32C are views for describing the variation state of birefringence depending the difference in incidence angle. The amount of birefringence of the sample such as an optically anisotropy crystal or a polymer material is considered while using a three-dimensional refractive index ellipsoid determined by the refraction indices nx, ny and nz on the X, Y and Z axes, respectively. If so, the amount of birefringence varies according to observation direction, that is, the difference of refraction index between the major axis and minor axis of the ellipsoid in a plane passing the origin of the refractive index ellipsoid and perpendicular to the observation direction occurs.

In other words, the direction of the refractive index ellipsoid differ, between a case where parallel light is vertically incident on the sample as shown in FIG. 32A and a case where parallel light is obliquely incident on the sample as shown in FIGS. 32B and 32C. As a result, there occur different phase differences of birefringence received by light differ as in the case of the different observation directions as stated above.

Then, consideration is given to a case where convergent light is incident on a sample using a lens system as shown in FIG. 33. In this case, light fluxes A and B having different incidence angles and positioned in the convergent light, for example, receive different retardations from the sample. Due to this, the amount of retardation received by the overall convergent light is the product of the phase differences received by respective very small light fluxes divided from the light flux. Thus, if convergent light is incident on a sample, the following disadvantages occur, i.e., a light incidence angle cannot be specified in a strict sense and the amount of birefringence of the sample cannot be precisely measured.

SUMMARY OF THE INVENTION

The present invention has been made in view of the conventional disadvantages stated above. It is, therefore, an object of the present invention to precisely measure the amount of birefringence of a target while enhancing spatial resolution.

To obtain the above object, the inventor of the present invention conducted various studies and examinations as to methods for microscopically measuring birefringence in a case where parallel light is incident on a sample.

To reduce the beam diameter of laser beam while the parallel light remains unchanged, for example, a method for arranging a pinhole on the incidence side of a photo detector may be assumed. In this case, however, the light travelling direction is deflected at the edge portion of the pinhole and phenomena such as interference and diffraction tend to occur. As a result, an interference fringe pattern having different phase information may be possibly projected onto the light-receiving surface of the photo detector. Due to this, it was found that a constant component of the light phase cannot be obtained and that it was difficult to obtain a precise amount of birefringence.

Considering this, in the method for reducing the beam diameter of laser beam without any influence of disturbances such as an optical interference phenomenon, a diffraction phenomenon and the like while the parallel light remains unchanged, attention was paid to the idea of taking part of light fluxes using an optical fiber and optically transmitting them.

A birefringence measurement optical system according to the present invention has been completed based on the above-stated idea and characterized by comprising a polarized light emission optical system emitting a light signal in a predetermined polarization state toward a target; a polarized light detection optical system detecting a light signal from the polarized light emission optical system through the target, the light signal including birefringence information on the target which can be polarimetrically analyzed; and a photo detector converting the light signal from the polarized light detection optical system into an electric signal and detecting the electric signal, and also characterized by arranging a light transmission path, preferably an optical fiber, for taking part of light fluxes of the light signal and transmitting the part of light fluxes from the target toward the photo detector, between the photo detector and the target.

As a preferred mode of the present invention, at least one of the following cases is adopted: 1) the optical fiber is arranged between the polarized light detection optical system and the photo detector; 2) the optical fiber is comprised of a core constituted by material having a predetermined photoelastic constant; 3) the optical fiber is arranged between the target and the polarized light detection optical system; 4) the optical fiber is provided with a sharpened tip end portion directed toward the target; 5) at least part of the polarized light detection optical system is integrally attached to the optical fiber; 6) the optical system further comprises a mechanism for freely scanning at least a target-side tip end portion of the optical fiber within the light fluxes of the light signal; and 7) the optical fiber is a plurality of optical fibers and the plurality of optical fibers are arranged in parallel.

The type of the optical fiber should not be specially limited and may be one of optical fibers such as commercially available optical fibers of various core diameters. If a plurality of optical fibers having different core diameters is aligned, for example, it is possible to measure birefringence with different spatial resolutions simultaneously. In addition, if an optical fiber having a smaller aperture diameter than those of commercially available optical fibers is required, the tip end portion of the optical fiber may be sharpened by a method such as a method of expanding the optical fiber to thereby make the aperture thinner.

A high spatial resolution polarimetric apparatus according to the present invention is characterized by comprising a birefringence measurement optical system using the above-stated light transmission path.

Preferably, the high spatial resolution polarimetric apparatus comprising: a birefringence measurement optical system for measuring birefringence information of a target to be measured; and analyzing means for analyzing at least one of a retardation, an azimuth angle of a principal axis and an optical rotation angle of the target based on the birefringence information measured by the birefringence measurement optical system. In this apparatus, the birefringence measurement optical system includes: a polarized light emission optical system emitting a light signal in a predetermined polarization state toward the target; a polarized light detection optical system detecting the light signal from the polarized light emission optical system through the target, the light signal including birefringence information on the target which can be polarimetrically analyzed; a photo detector converting the light signal from the polarized light detection optical system into an electric signal and detecting the electric signal; and a light transmission path arranged between the target and the photo detector, the light transmission path taking part of light fluxes of the light signal at a target side thereof and transmitting the part of light fluxes from the target side toward a photo detector side thereof.

BRIEF DESCRIPTION OF THE DRAWINGS

The accompanying drawing which are incorporated in and constitute a part of this specification, illustrate embodiments of the present invention and, together with the description, serve to explain the principles of the present invention; in which:

FIGS. 32A, 32B and 32C are views for describing the variation state of birefringence depending on the difference in incident angle according to the conventional system, where FIG. 32A is a conceptual view in case of normal incidence and FIGS. 32B and 32C are conceptual views in case of oblique incidence.

DESCRIPTION OF THE PREFERRED EMBODIMENTS

Now, the embodiments of birefringence measurement optical systems and high spatial resolution polarimetric apparatuses according to the present invention will be described with reference to the accompanying drawings.

First Embodiment

The first embodiment will be described with respect to FIGS. 1 to 4.

Figure 1:
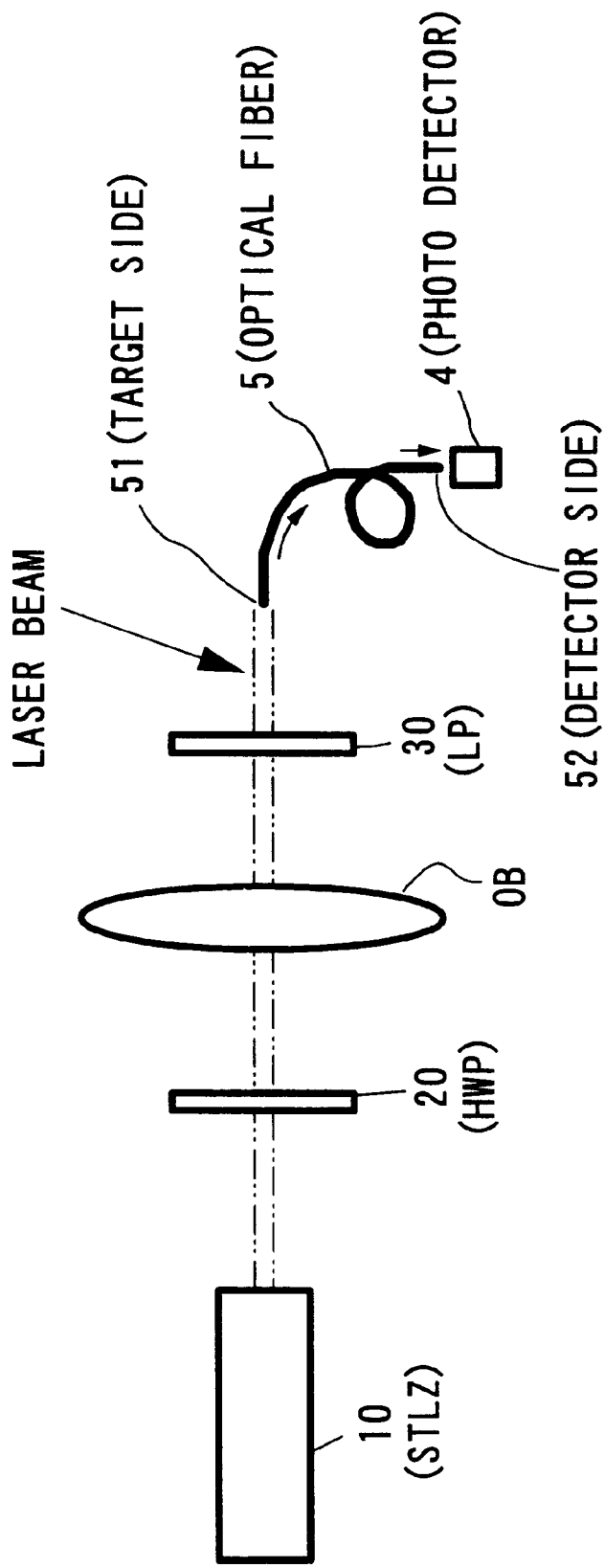
FIG. 1 is a conceptual view showing the overall constitution of a birefringence measurement optical system in the first embodiment according to the present invention.

In FIG. 1, a birefringence measurement optical system of this embodiment applies a birefringence measurement optical system, for example, proposed by Japanese Patent Application Laid-Open No. 8-327498, for ensuring a wide dynamic range for measuring birefringence.

In this measurement optical system shown in FIG. 1, linearly polarized light orthogonally intersecting two frequencies generated by a Stabilized Transverse Zeeman Laser (to be referred to as "STZL" hereinafter) is applied onto a sample (target) OB through a halfwave plate (HWP) 20, a transmitted light is detected as a light signal indicating information on a retardation, an azimuth angle of a principal axis and an optical rotation angle of the sample OB which can be polarimetrically analyzed through a linear polarizer (LP) 30 by a photo detector 4 such as a photodiode and the like. An optical fiber 5 (corresponding to a light transmission path of the present invention) is arranged between a linear polarizer 30 and the photo detector 4 in the birefringence measurement optical system.

Now, the principle of measurement of birefringence using the optical fiber 5 will be described.

Figure 2:
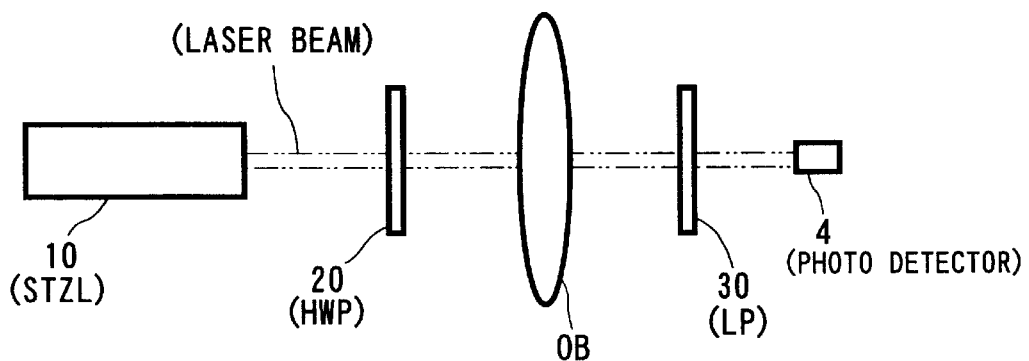
FIG. 2 is a conceptual view showing a conventional birefringence measurement optical system for describing the principle of birefringence measurement.
Figure 3:
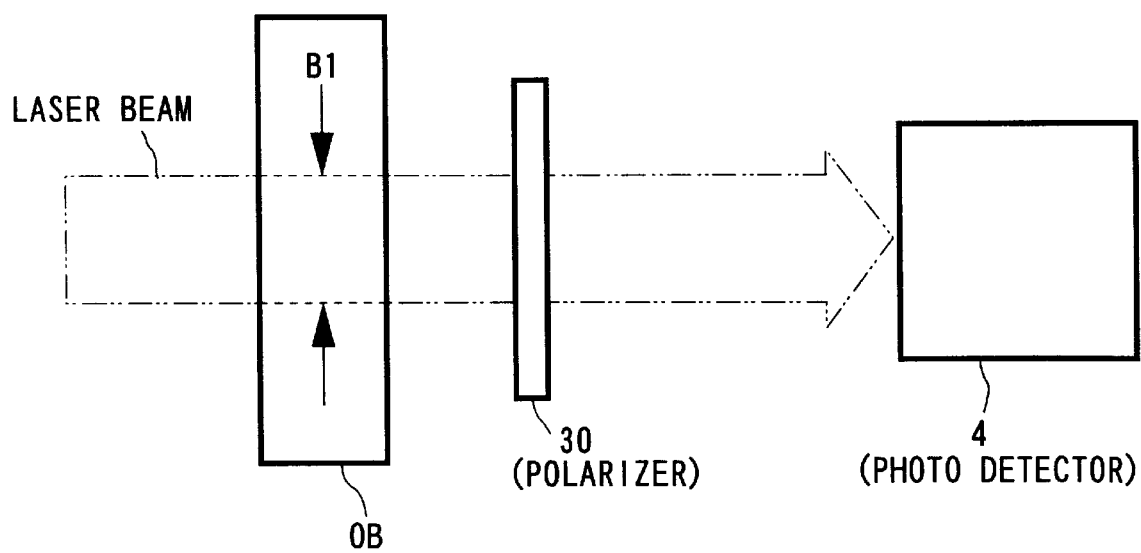
FIG. 3 is a conceptual view for describing spatial resolution in the conventional system.

First, in a case where the optical fiber 5 is not arranged, a portion corresponding to the entire range of a laser beam is directly incident on the photo detector 4 as shown in FIGS. 2 and 3. Due to this, the spatial resolution for birefringence measurement is a region B1 determined by the beam width of the laser beam as shown in FIG. 3. In that case, it is difficult to measure a birefringence distribution in a very small area within the beam.

Figure 4:
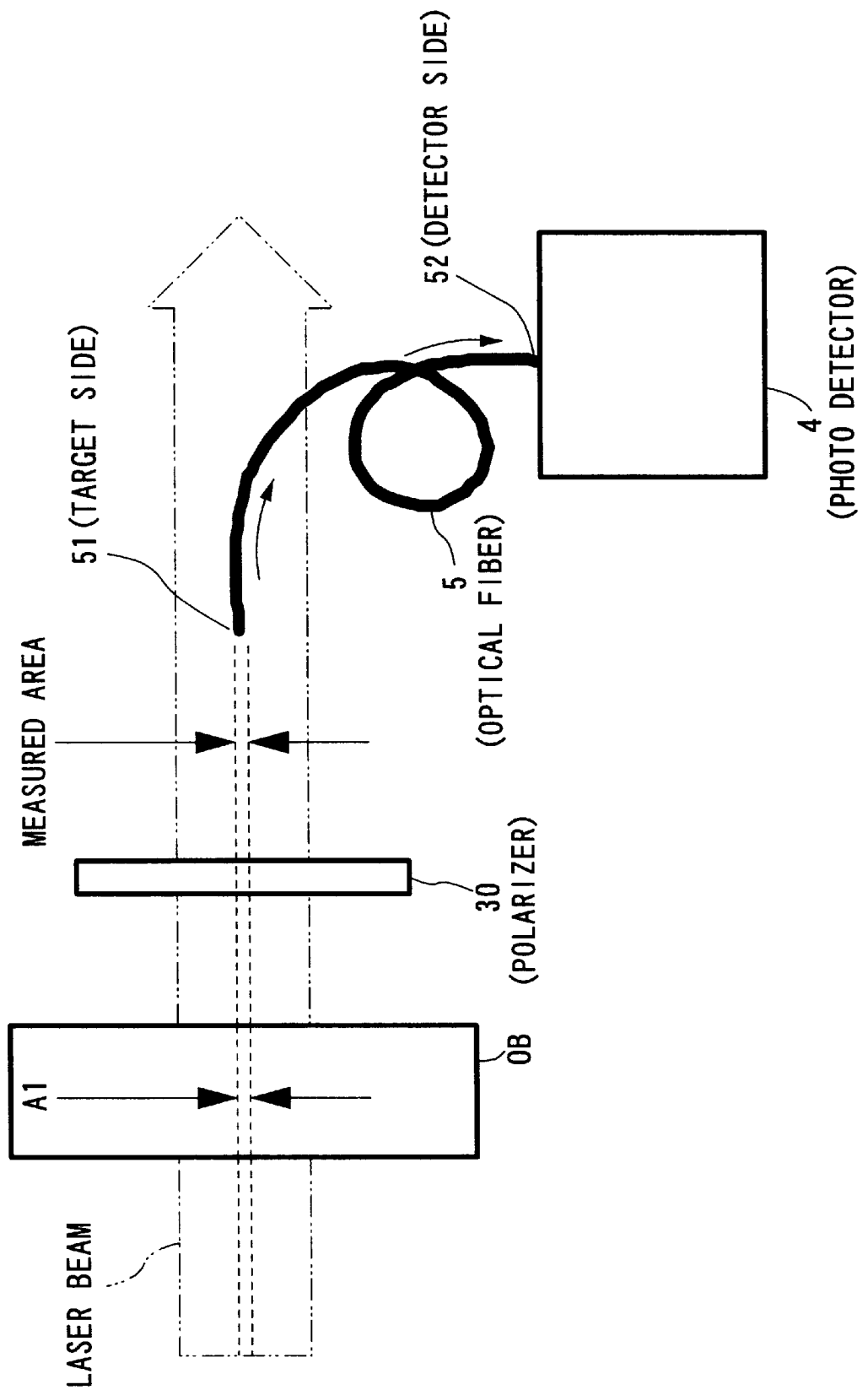
FIG. 4 is a conceptual view for describing spatial resolution if an optical fiber is used according to the present invention.

Next, in a case where the optical fiber 5 is arranged, part of laser beam from the linear polarizer 30 is fetched by the aperture portion of the optical fiber 5 inserted into the laser beam. Then, the part of laser beam taken by the optical fiber 51 passes through the fiber 5 from a target side (light source side) 51 to a detector side 52 of the fiber 5. Then, a photo detector 4 as shown in FIG. 4 detects the part of laser beam passing through the fiber 5. The light signal measured herein is part of a light flux taken out with almost the same thickness as the diameter of the aperture portion of the optical fiber 5. If a laser beam is, for example, parallel, the measurement range for the sample OB is equal to the aperture diameter of the optical fiber 5, i.e., a range A1 shown in FIG. 4.

Accordingly, in this embodiment, since the optical fiber 5 is arranged, it is possible to transmit only the intensity of the light signal taken out from the optical fiber 5 to the photo detector 4 while giving a limitation so as to improve the spatial resolution for birefringence measurement using the aperture diameter, without the influence of disturbances such as diffraction and interference phenomena. Although the optical fiber 5 has a property of changing a polarization state, the property is almost negligible. The constituent elements which should take account of the polarization state for birefringence measurement are the STZL 10, the halfwave plate 20 and the linear polarizer 30 in the arrangement of this optical system.

In this embodiment, since the birefringence information on the to-be-measured sample is included only in the intensity change of the light signal which has passed through the linear polarizer, the optical fiber is arranged between the polarizing element proximate to the photo detector and functioning based on the birefringence measurement principle and the photo detector. It is noted that the present invention should not be limited thereto. A lens system can be interposed between the optical fiber and the photo detector if it is specially required in view of light condensing characteristics or if light intensity is low and detection sensitivity cannot be increased.

In this embodiment, the STZL 10, the halfwave plate 20 and the linear polarizer 30 are employed as a birefringence measurement optical system into which the optical fiber should be arranged. The present invention should not be limited thereto.

Figure 5:
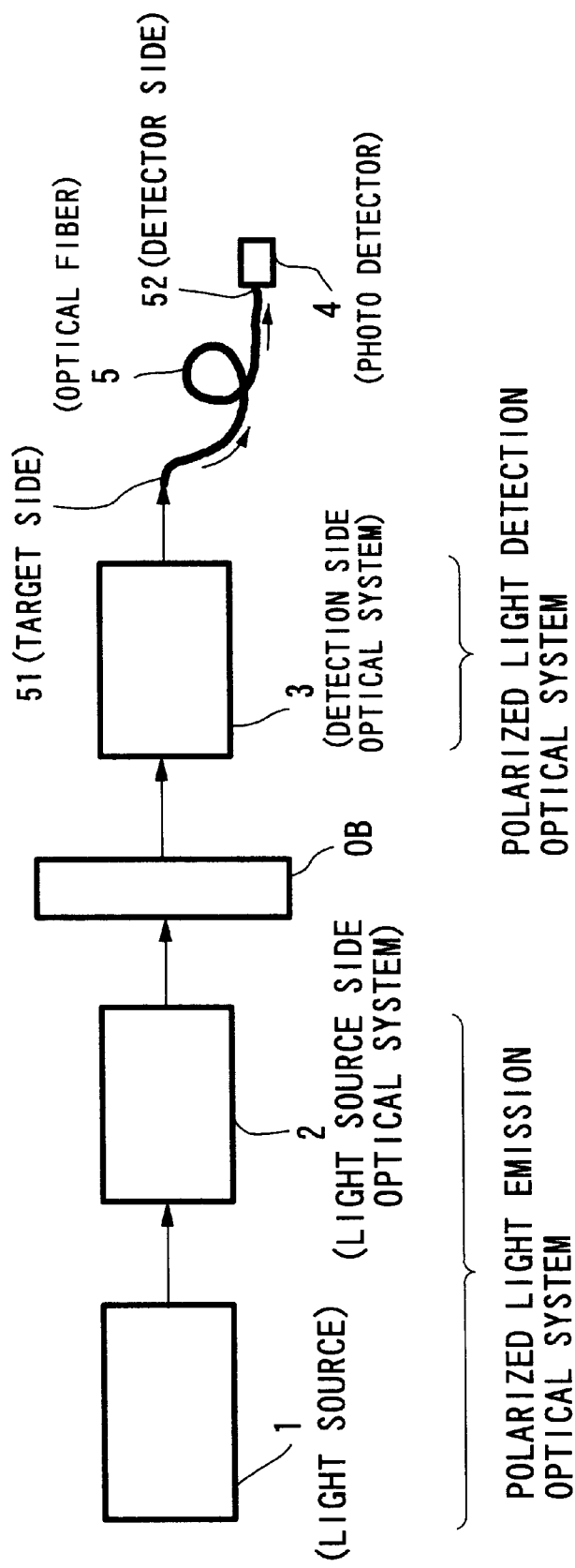
FIG. 5 is a conceptual view of a birefringence measurement optical system embodying the highest concept according to the present invention.

A birefringence measurement optical system shown in, for example, FIG. 5 embodies the highest concept of the basic constitution based on the birefringence measurement principle of the present invention. This optical system is comprised of a light source 1, a light source side optical system 2, and a detection side optical system 3, a photo detector 4, and an optical fiber 5 (corresponding to a light transmission path of the present invention).

In the optical system in FIG. 5, the light source 1 includes at least one of, for example, a laser such as the above-stated STZL 10, a white light source, a combination of a white light source and a spectroscope (or spectrograph), a combination of a white light source and a wavelength selection filter or the like. The light source side optical system 2 includes all the optical elements disposed between the light source 1 and the sample OB, for example, the above-stated halfwave plate 20. The detection side optical system 3 includes all the optical elements disposed between the sample OB and the photo detector 4, for example, the above-stated linear polarizer 30. It is noted that the light source 1 and the light source side optical system 2 correspond to a polarized light emission optical system and the detection side optical system 3 corresponds to a polarized light detection optical system according to the present invention.

Specific examples for applying the light source 1, the light source side optical system 2 and the detection side optical system 3 may be not only the above-stated constitution (the STZL 10, halfwave plate 20 and linear polarizer 30) but also one of or a combination of the embodiments shown in, for example, FIGS. 6 to 13 to be described hereinafter, wherein elements similar to the above-stated embodiments are denoted by the same reference numerals, and the explanation thereof is simplified or omitted.

Figure 6:
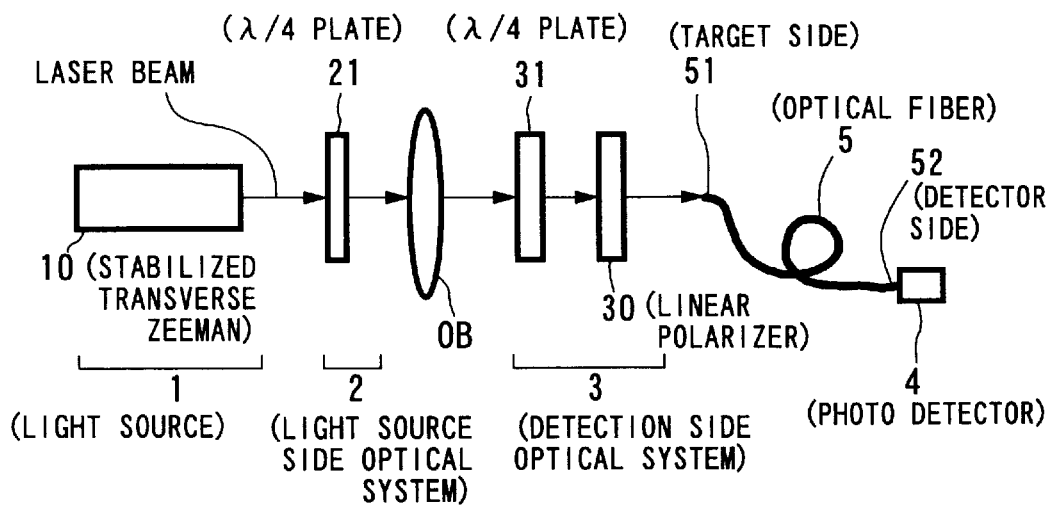
FIG. 6 is a conceptual view of a birefringence measurement optical system if a λ/4 plate and the like are used according to the present invention.

A measurement optical system shown in FIG. 6 adopts a high speed birefringence measurement method (described in, for example, Japanese Patent Application Laid-Open No. 8-254495) employing an STZL 10 as a light source 1, λ/4 plate 21 as a light source side optical system 2, λ/4 plate 31 and a linear polarizer 30 as a detection side optical system 3.

Figure 7:
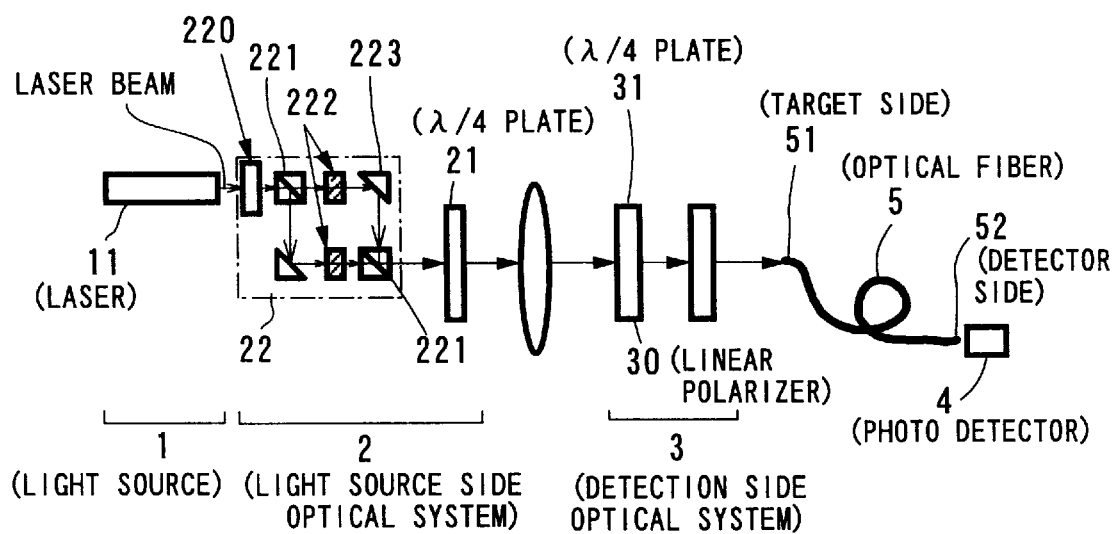
FIG. 7 is a conceptual view of a birefringence measurement optical system if a frequency shifter or the like is used according to the present invention.

A measurement optical system shown in FIG. 7 employs a laser 11 as a light source 1, a frequency shifter (consisted by a linear polarizer, a beam splitter, an acoustic optical element (AOM), a reflection mirror and the like) 22 and a λ/4 plate 21 as a light source side optical system 2, and a λ/4 plate 31 and a linear polarizer 30 as a detection side optical system 3. The optical system shown in FIG. 7 differs from that shown in FIG. 6 in that the frequency shifter 22 formed by combining acoustic optical elements instead of the STZL 10 and the ordinary laser 11 are used in FIG. 7.

Figure 8:
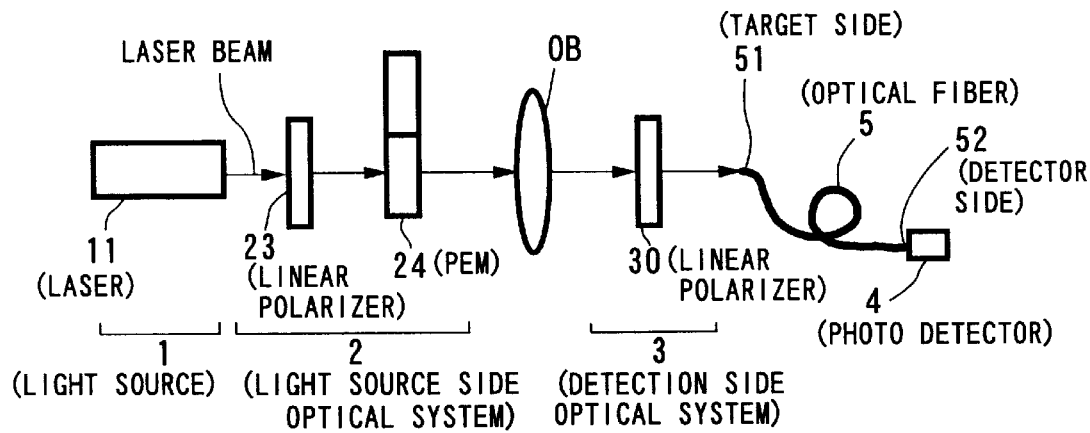
FIG. 8 is a conceptual view of a birefringence measurement optical system if a photoelastic modulation device and the like are used according to the present invention.
Figure 9:
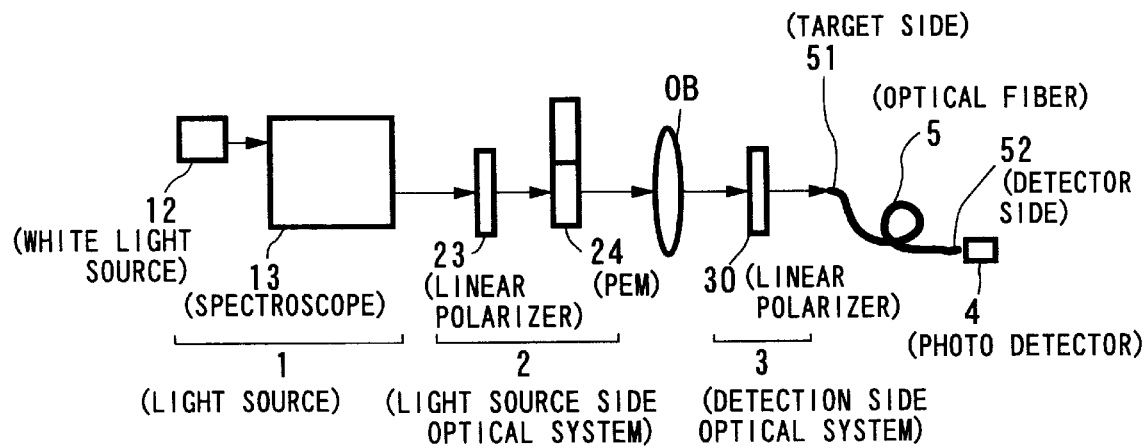
FIG. 9 is a conceptual view of a birefringence measurement optical system if a white light source and the like are used according to the present invention.

A measurement optical system shown in FIG. 8 employs a laser 11 as a light source 1, a linear polarizer 23 and a photoelastic modulation element (PEM) 24 as a light source side optical system 2 and a linear polarizer 30 as a detection side optical system 3. In this case, the optical system may be constituted such that a combination of a white light source 12 and a spectroscope (or spectrograph) 13 instead of the laser 11 is used as the light source 1 as shown in FIG. 9.

Figure 10:
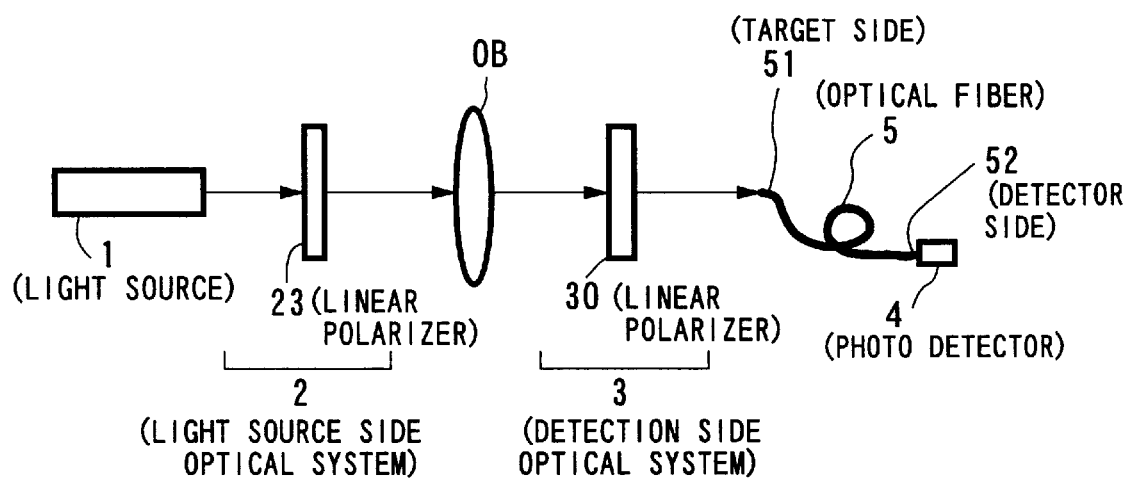
FIG. 10 is a conceptual view of a birefringence measurement optical system if linear polarizers are used on both sides of a sample according to the present invention.
Figure 11:
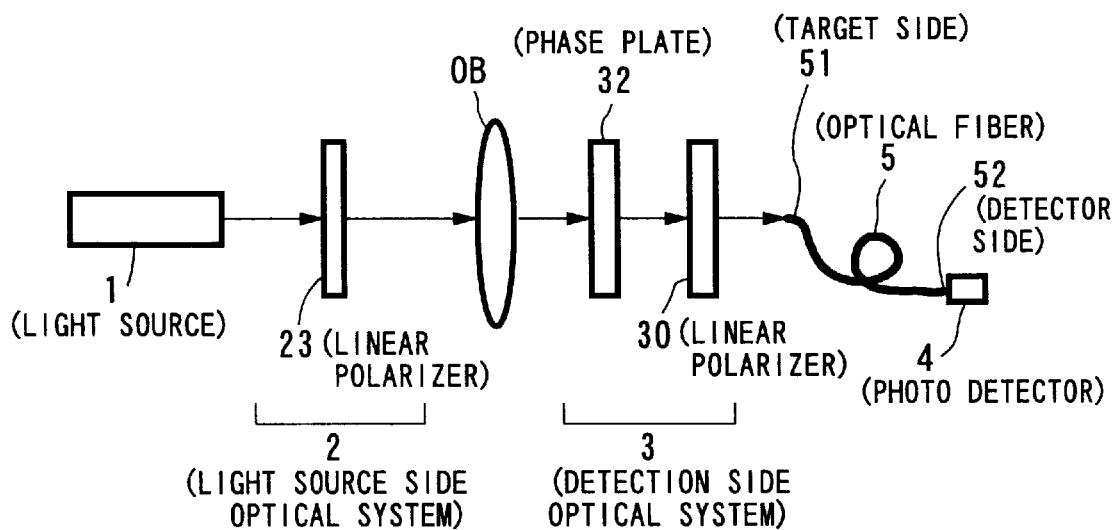
FIG. 11 is a conceptual view of a birefringence measurement optical system if a phase plate is used on the detector side according to the present invention.
Figure 12:
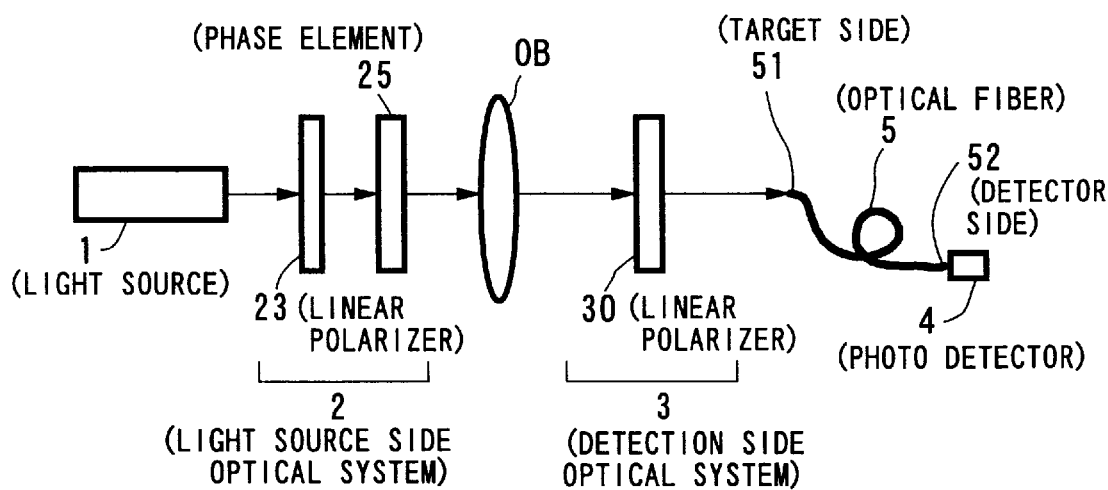
FIG. 12 is a conceptual view of a birefringence measurement optical system if a phase plate is used on the light source side according to the present invention.
Figure 13:
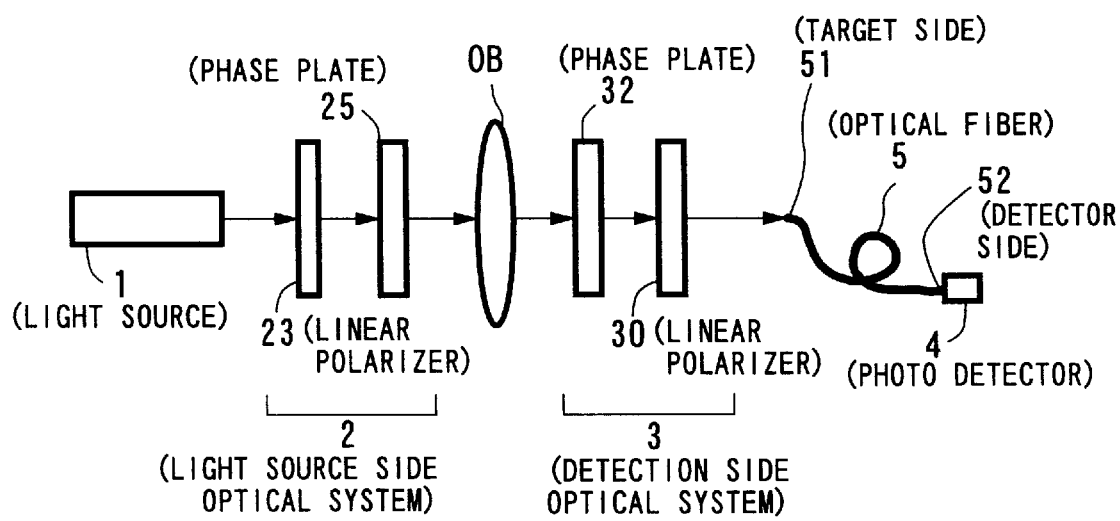
FIG. 13 is a conceptual view of a birefringence measurement optical system if phase plates are used on both sides of a sample according to the present invention.

A measurement optical system shown in FIG. 10 adopts, for example, a method using a rotating analyzer or a method using a rotating polarizer and employs a linear polarizer 23 as a light source side optical system 2 and a linear polarizer 30 as a detection side optical system 3. As modified examples of the system shown in FIG. 10, a case where a phase plate 32 is arranged between the sample OB and the linear polarizer 30 as shown in FIG. 11, a case where a phase plate 25 is arranged between the sample OB and the linear polarizer 23 as shown in FIG. 12, a case where two phase plates 25 and 32 are arranged (see FIG. 13) and the like may be applicable.

Figure 14:
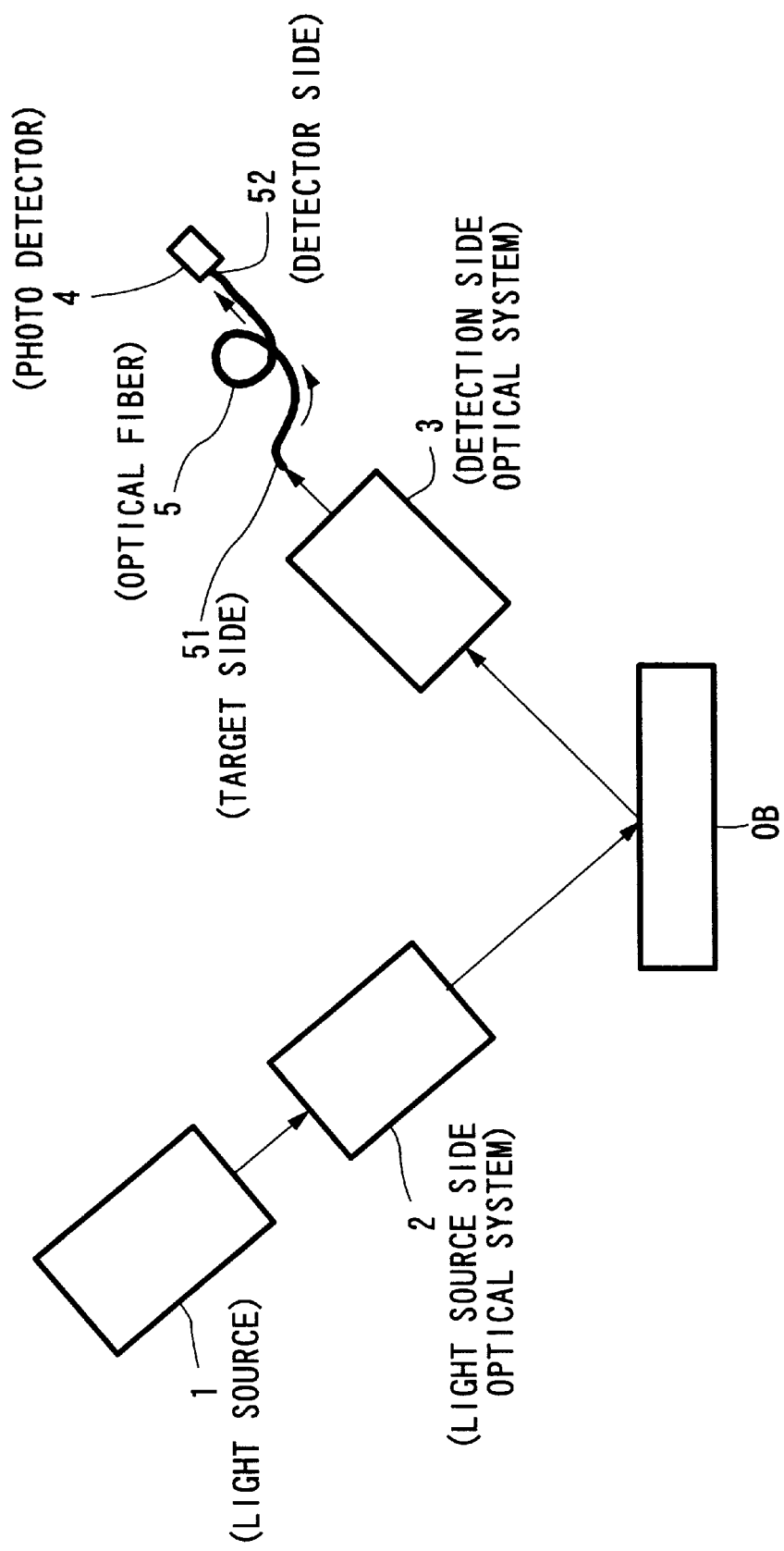
FIG. 14 is a conceptual view of a birefringence measurement optical system if a reflection light is detected according to the present invention.

Although the first embodiment employs the optical arrangement for measuring the transmitted light of the sample, the present invention should not be limited to thereto. As show in, for example, FIG. 14, a detection side optical system 3, an optical fiber 4 and a photo detector 5 may be arranged at positions at which the reflection light of the sample is measured. The constitution for measuring a reflection light stated above is more effective if a sample or the like hardly transmits light.

Second Embodiment

The second embodiment will be described with respect to FIGS. 15 to 20, wherein elements similar to the above-stated embodiment are denoted by the same reference numerals, and the explanation thereof is simplified or omitted.

Figure 15:
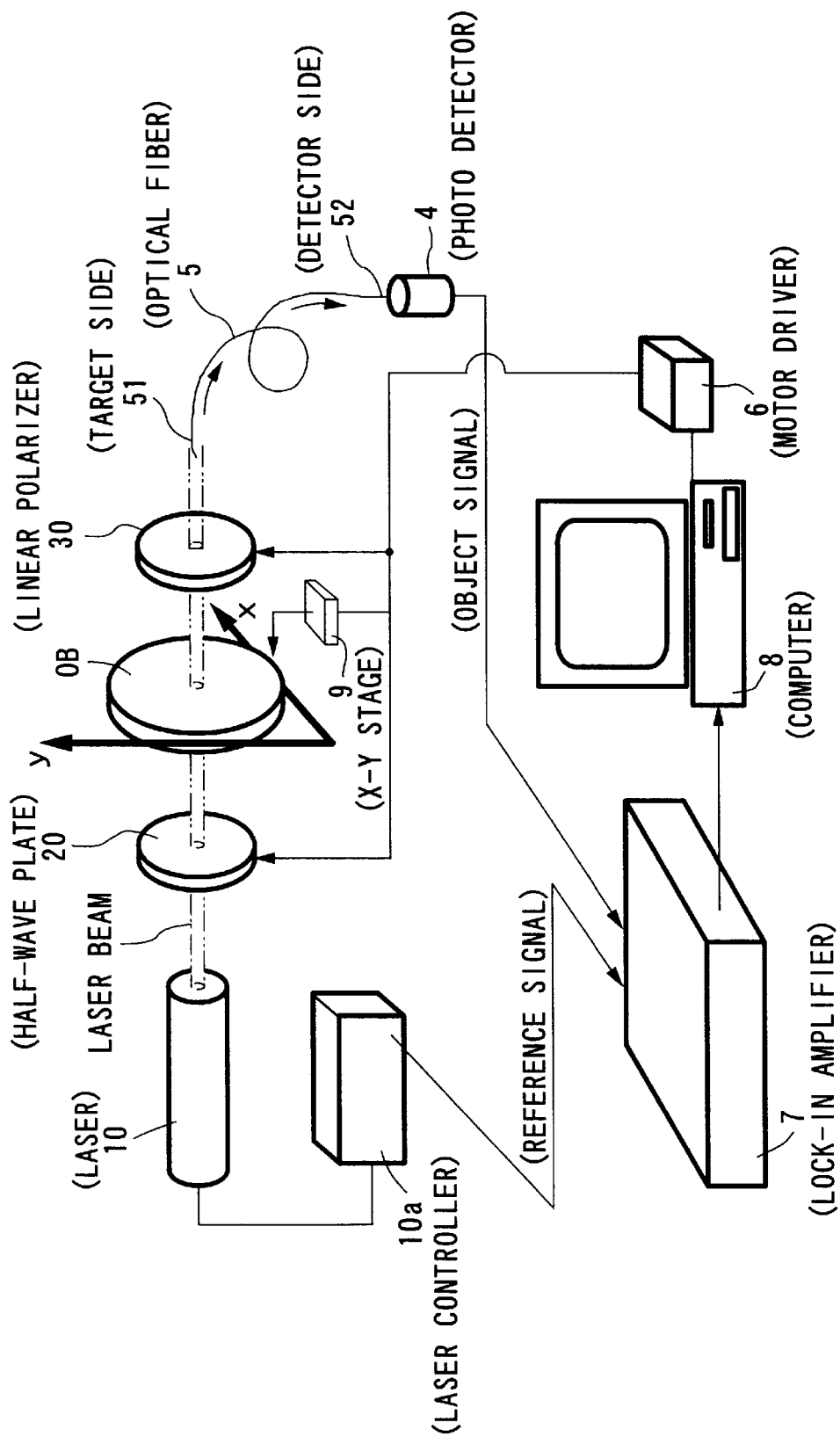
FIG. 15 is a conceptual view showing the overall constitution of a high spatial resolution polarimetric apparatus in the second embodiment according to the present invention according to the present invention.

A high spatial resolution polarimetric apparatus shown in FIG. 15 applies a birefringence measurement apparatus, for example, proposed by the Japanese Patent Application Laid-Open No. 8-327498 as in the case of the first embodiment. The apparatus comprises a motor driver 6 on the rotation of a halfwave plate 20 and on that of a linear polarizer 30 and a lock-in amplifier 7 for signal processing, a computer 8 for data operation, an XY stage 9 for mounting a sample thereon and a laser controller 10a for an STZL in addition to the above-stated birefringence optical system (the laser beam source (STZL 10), the halfwave plate 20 and the linear polarizer 30).

This polarimetric apparatus takes out a sine wave signal and a cosine wave signal of the component of an alternate current having the same frequency as that of a reference signal obtained by the laser controller 10a, from a detection signal detected by the photo detector 4 by means of the signal processing of the lock-in amplifier 7, and obtains the retardation, azimuth angle of principal axis and optical rotation angle of the sample OB by the operational processing of the computer 8 based on the processed signals.

Next, a verification experiment was conducted to confirm the effectiveness of the polarimetric apparatus, which employs the optical fiber 5. In this measuring experiment, a Babinet-Soleil compensator (to be referred to as "BSC" hereinafter) which is an optical element which amount of birefringence is variable was used as a sample OB and the correlation between one of the set values of the amount of birefringence and azimuth angle of principal axis of the BSC, when changed in a linear function manner, and a measurement value was examined.

Figure 16:
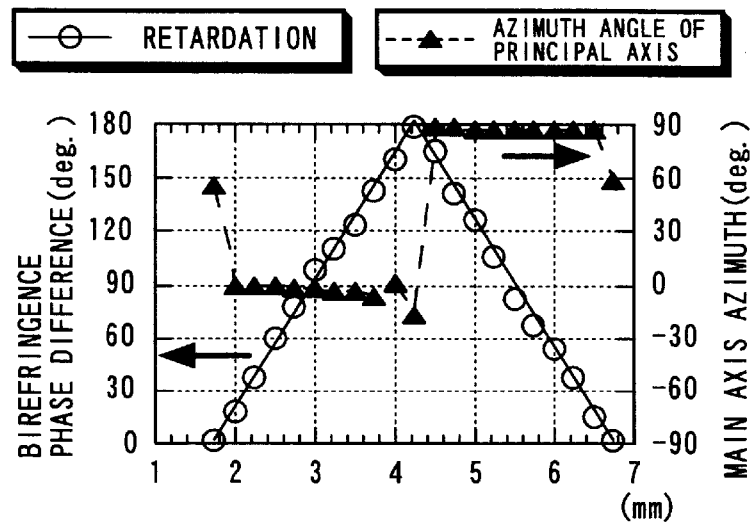
FIG. 16 is a graph for describing the result of an experiment if the amount of birefringence of a BSC was changed.
Figure 17:
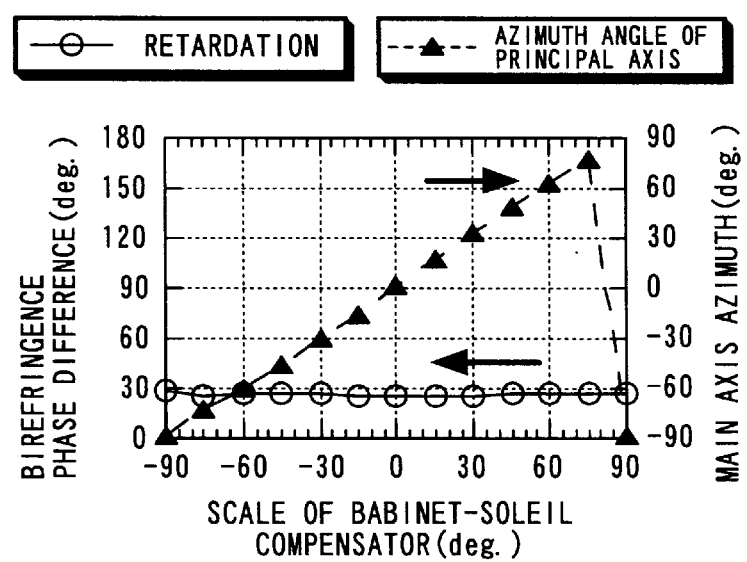
FIG. 17 is a graph for describing the result of an experiment if the azimuth angle of principal axis of the BSC was changed.
Figure 18:
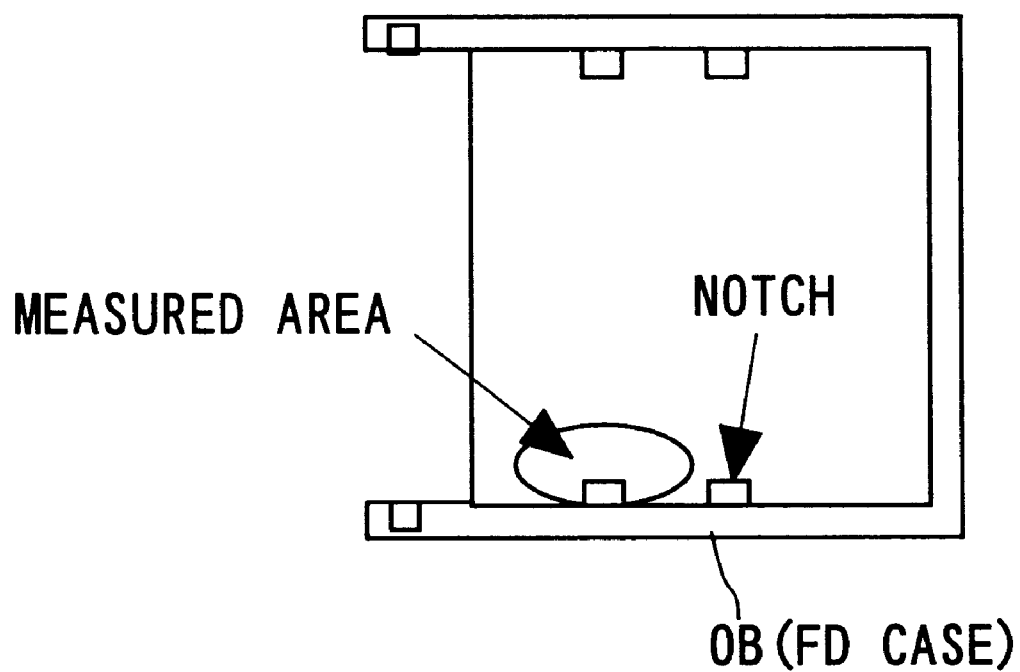
FIG. 18 is a schematic diagram of a FD case used in a verification experiment.

FIG. 16 is a view for describing a case where the amount of birefringence of the BSC is changed. In the case of FIG. 16, the measurement value was changed linearly with respect to the set value of the BSC, thereby confirming that these values strongly correlate to each other. In this case, the amount of birefringence turns down at 180 degrees. While the measurement was conducting, assuming that the azimuth angle of principal axis is reversed, i.e., changed by 90 degrees, almost the correct values could be obtained physically. In the case of FIG. 17 where the azimuth angle of principal axis of the BSC was changed, it was confirmed that the set value of the BSC strongly correlate to a measurement value, as well.

The measuring experiment demonstrated that the high spatial resolution birefringence measurement method using the optical fiber 5 is effective not only in principle but also in the actual situation and that a birefringence distribution could be measured with high spatial resolution by, for example, two-dimensionally scanning the irradiation spot of a laser beam on the sample.

Considering this, an experiment was conducted to examine the effectiveness of this high spatial resolution birefringence measurement. In this measuring experiment, an acrylic floppy disk case (to be referred to "FD case" hereinafter) shown in FIG. 18 was used as a sample OB and a protruding notch portion formed on the edge portion within the case was selected as a measurement portion for the FD case.

The birefringence of the notch portion is suddenly changed in a direction of molecular or dipole of molecular chain of polymer during the formation of the notch portion. This change was clearly observed as the change of a hue by an observation unit using a tint color plate method, which has been conventionally known as a simple birefringence observation method. In the tint color plate method, it is observed that the portion which hardly shows birefringence is a reddish purple color, the portion which shows birefringence is a color changed in hue from the reddish purple color. While using the notch portion of the FD case showing such birefringence as a measured area (see FIG. 18) and birefringence was measured. For comparison purposes, the same measurement was conducted by the conventional method. The results are shown in FIGS. 19 and 20, respectively.

Figure 19:
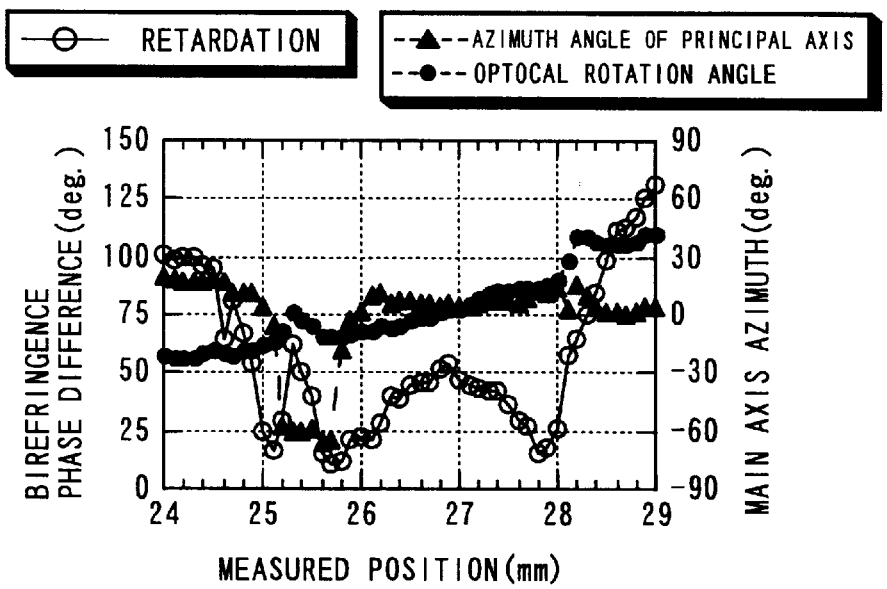
FIG. 19 is a graph for describing the result of an experiment if an optical fiber is used according to the present invention.
Figure 20:
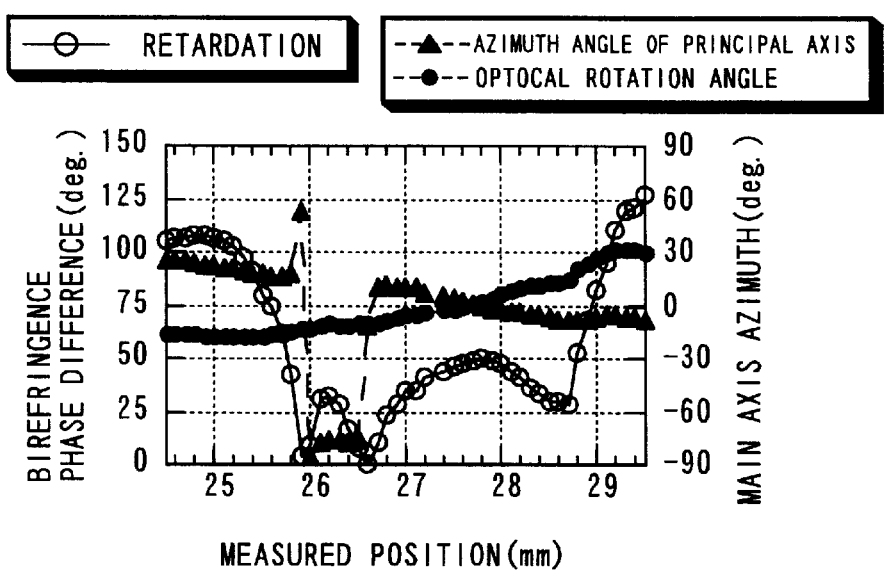
FIG. 20 is a graph for describing the result of an experiment according to the conventional system.
Figure 21:
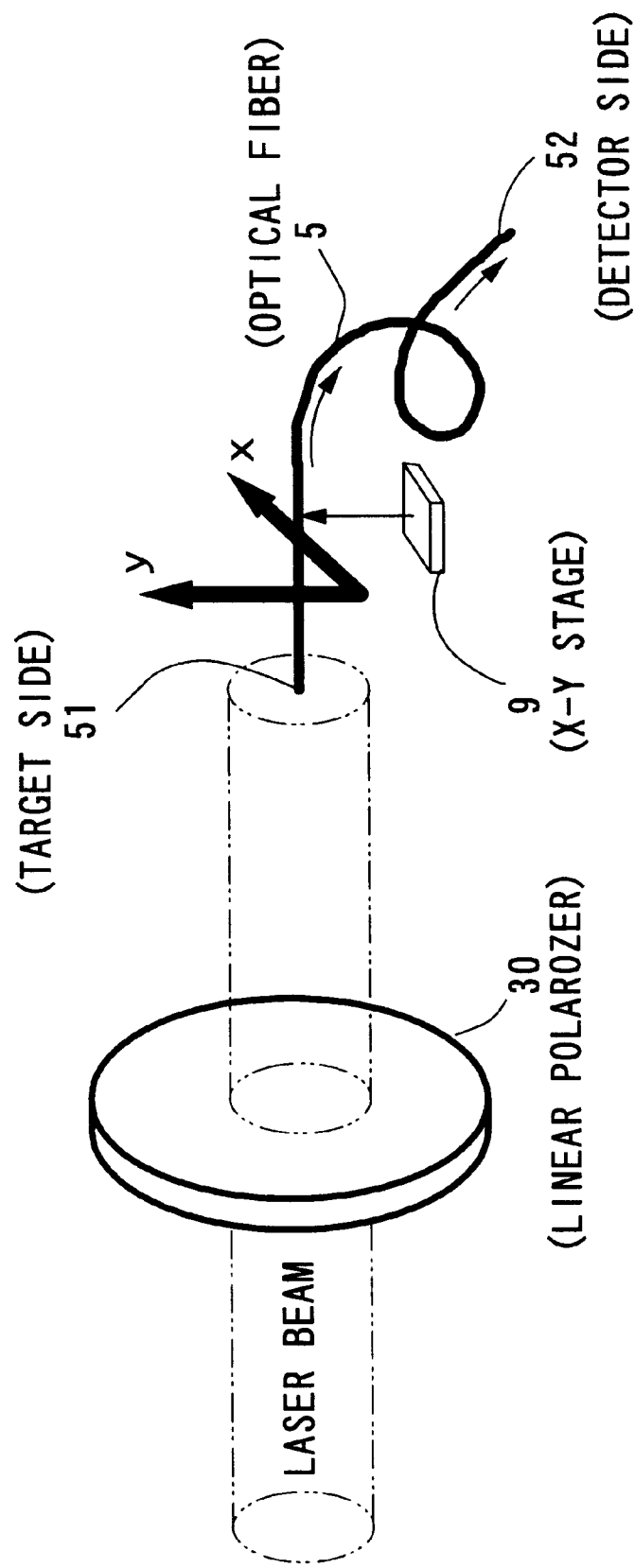
FIG. 21 is a conceptual view for describing the important parts of an optical system if an optical fiber is scanned according to the present invention.

FIG. 19 is a view for describing the optical fiber detection method and FIG. 20 is a view for describing the conventional method. Here, if the birefringence of the sample is large and the sample is orientated such that molecules are twisted, it normally means that not only birefringence but also optical rotation properties are shown. As a result, it was confirmed that the measurement values (a retardation, an azimuth of a main axis and an optical rotation angle) were more variable if using the optical fiber shown in FIG. 19 than those in the conventional method shown in FIG. 20 and that the variation state of the birefringence was measured with slightly finer precision. The same experiment was repeated several times. Any experiment showed the same trend.

In this embodiment, the method of scanning a sample relative to the XY stage is adopted. The present invention should not be limited thereto and may use a method of scanning an optical fiber within a beam. In case of scanning a very small range, in particular, a relatively expensive scanning stage is required to precisely drive a large sample. Due to this, the method of scanning the optical fiber 5 as shown in, for example, FIG. 5 is preferable. If this method is used, the XY stage is secondary made smaller in size to thereby advantageously enhance positioning precision.

Third Embodiment

The third embodiment will be described with respect to FIG. 22, wherein elements similar to the above-stated embodiments are denoted by the same reference numerals, and the explanation thereof is simplified or omitted.

If an ordinary optical fiber is used, an internal stress is generated by the bending of the fiber or the like. A photoelastic effect following the internal stress causes a change in the polarization state when a light signal passes through the optical fiber. Due to this, the arrangement position is substantially limited to between the detection side optical system and the photo detector as stated above. This third embodiment is intended to contrive material for the optical fiber to thereby increase alternatives for the arrangement position.

Figure 22:
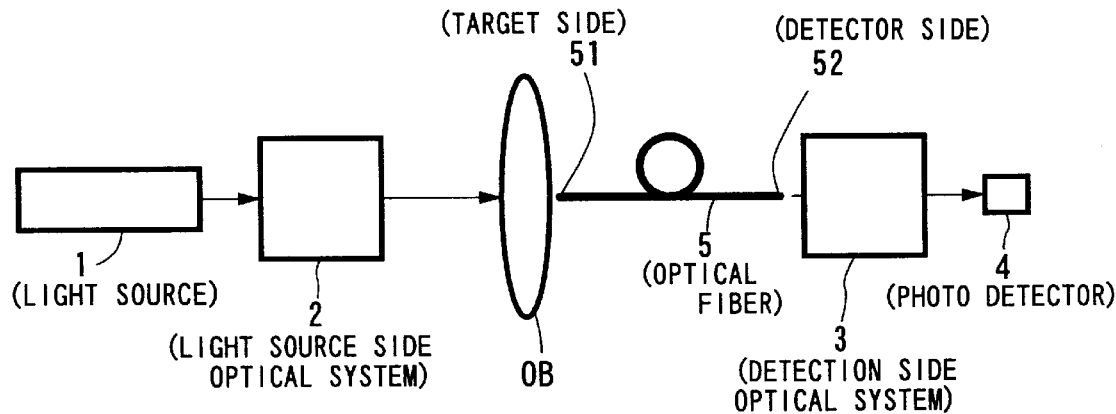
FIG. 22 is a conceptual view of a birefringence measurement optical system if an optical fiber is arranged between a sample and a detection side optical system according to the present invention.

Namely, in a birefringence measurement optical system shown in FIG. 22, material which has a photoelastic constant of zero or small value which does not have a great effect on the polarization state, such as material having a core constituted by, for example, glass rich in lead content (lead-rich glass) is used for an optical fiber 5, thereby allowing the optical fiber 5 to be arranged between the sample OB and the detection side optical system 3.

Since the optical fiber can be arranged proximate to the sample, this embodiment has advantage in that a measured position can be determined more precisely by observing the sample macroscopically or microscopically.

Figure 23:
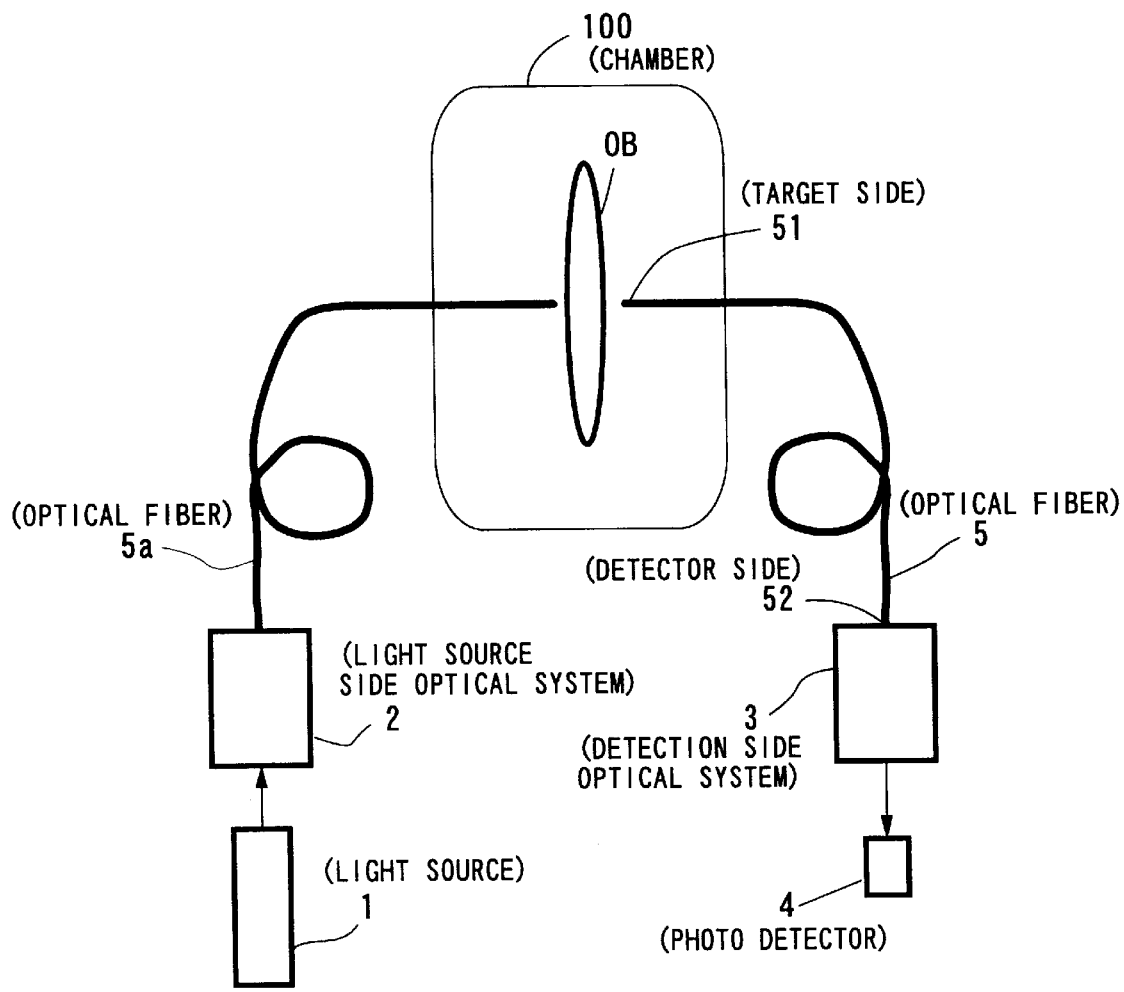
FIG. 23 is a conceptual view of a birefringence measurement optical system if an optical fiber is arranged between a sample and a light source side optical system also according to the present invention.

In a birefringence measurement system shown in FIG. 23 as another mode, an optical fiber 5a is also disposed between a light source side optical system 2 and a sample OB. This case has advantage of capable of changing the positional relationship between the optical elements for birefringence measurement and the sample more flexibly in addition to the above-stated advantage. As a result, even if the sample OB is put within a chamber 100 in FIG. 23 such as a vacuum device, a heat treatment device, an oil bath or the like, it is possible to measure birefringence, whereby various characteristics such as the birefringence dependence on temperature can be measured more easily.

Fourth Embodiment

The fourth embodiment will be described with respect to FIG. 24, wherein elements similar to the above-stated embodiments are denoted by the same reference numerals, and the explanation thereof is simplified or omitted.

Generally speaking, if a light beam is focused on a sample using a lens, spatial resolution on the sample increases; however, an accurate amount of birefringence cannot be obtained due to the different incidence angles of light fluxes within the beam with respect to the sample. Considering this, this embodiment is intended to allow birefringence to be measured using an optical fiber even if such a focusing lens is used.

Figure 24:
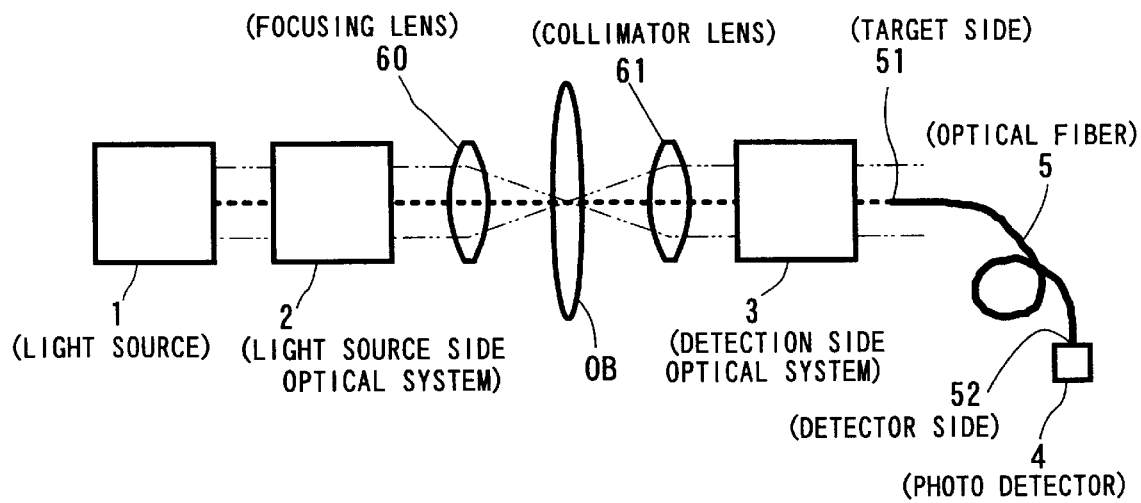
FIG. 24 is a conceptual view of a birefringence measurement optical system if a focusing lens is used according to the present invention.

A birefringence measurement optical system shown in FIG. 24 is constituted by arranging a focusing lens 60 between a light source side optical system 2 and a sample OB and a collimator lens 61 between the sample OB and a detection side optical system 3. Light flux which have passed through the sample are converted to parallel light by the collimator lens 61 and only the light fluxes passing straight through the sample OB are selected by an optical fiber 5 disposed on the optical axis.

Since a light beam can be applied only to a limited region on the sample, this embodiment is particularly effective if the sample has a structure to have a refraction index and the light diffraction or the like thereby occurs. The reason is that if a parallel light beam is incident on the sample, the light beam is applied to a region outside the measurement range and a diffracted light from the region applied with light is possibly incident on the optical fiber as a noise source of a signal. That is, if a small irradiation spot of a light beam is formed on the sample, it is possible to advantageously prevent the measurement of excessive light signals from the region outside the measurement range. By forming a light spot on the sample, it is possible to advantageously observe the measured position more easily.

Figure 25:
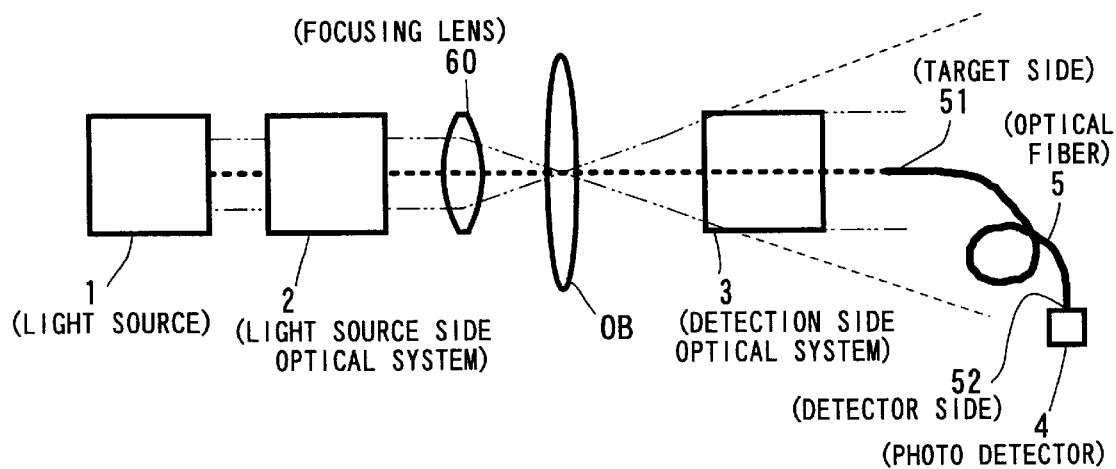
FIG. 25 is a conceptual view of another birefringence measurement optical system if a focusing lens is used according to the present invention.

A birefringence measurement optical system shown in FIG. 25 does not employ a collimator lens stated above but only employ a focusing lens 60. In the system shown in FIG. 25, only the center of the spread of the light signal from the sample OB, i.e., only light fluxes on the optical axis pass straight and the light in the very small region on the optical axis can be, therefore, regarded as parallel light. Thus, this embodiment can obtain the same advantages as those mentioned above.

Fifth Embodiment

The fifth embodiment will be described with respect to FIG. 26, wherein elements similar to the above-stated embodiments are denoted by the same reference numerals, and the explanation thereof is simplified or omitted.

Figure 26:
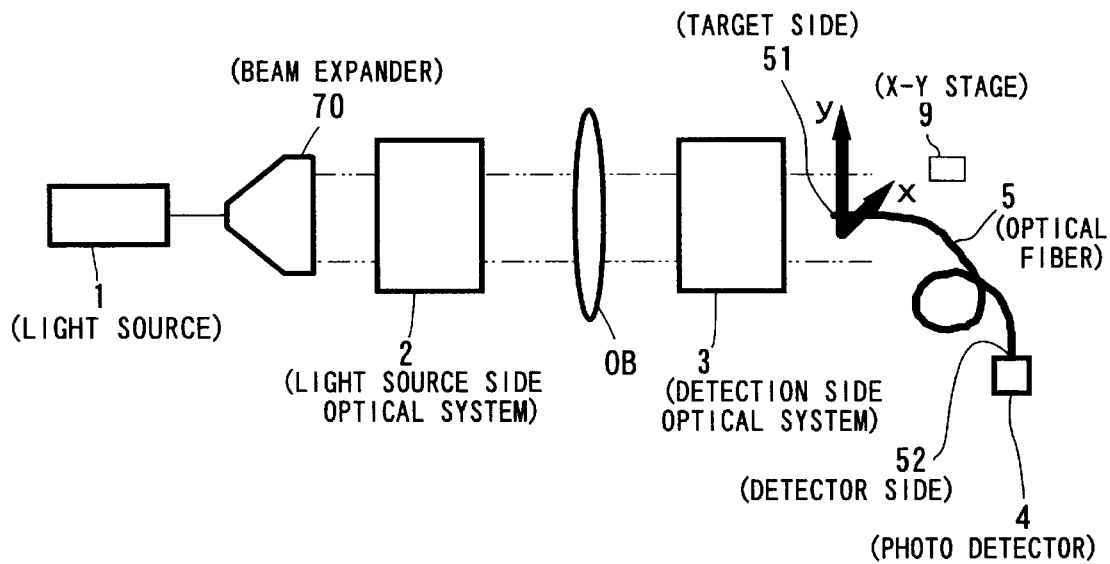
FIG. 26 is a conceptual view of a birefringence measurement optical system if a beam expander is used according to the present invention.

In a birefringence measurement optical system shown in FIG. 26, a beam expander 70 which functions to increase the beam width of incident light and to output parallel light fluxes, is arranged between a light source 1 and a light source side optical system 2, and an optical fiber 5 is two-dimensionally scanned relative to an XY stage 9 to thereby obtain the two-dimensional distribution of the birefringence of a sample OB.

If the beam expander 70 is used, the optical system has advantage in that the light irradiation area on the surface of the sample can be increased to thereby widen a range measurable with one scanning operation.

Figure 27:
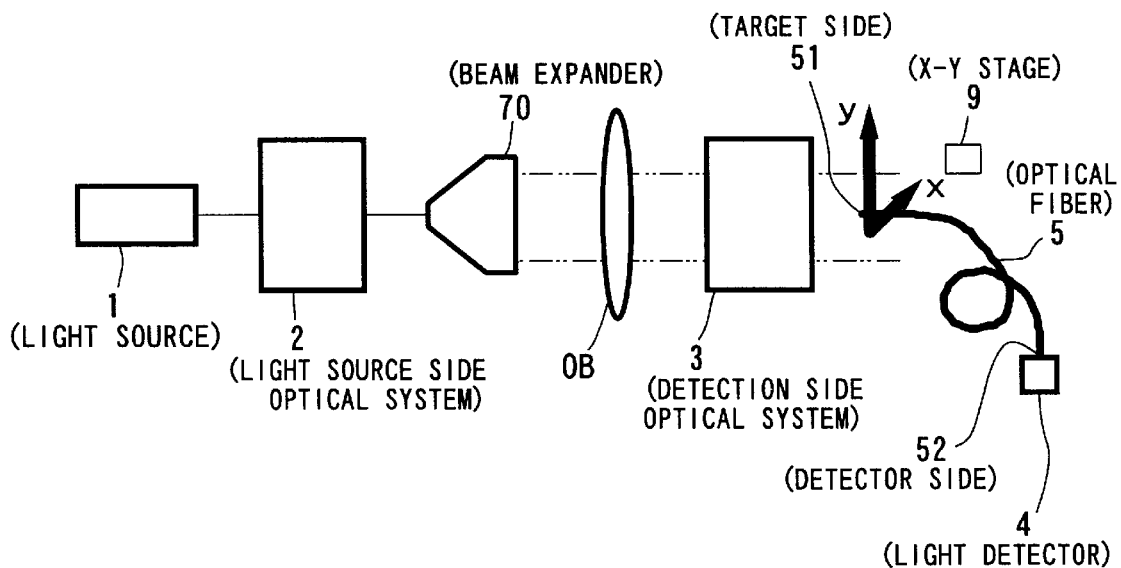
FIG. 27 a conceptual view of a birefringence measurement optical system if the arrangement position of the beam expander is changed according to the present invention.

In this embodiment, the beam expander is arranged between the light source and the light source side optical system. The present invention should not be limited thereto and can obtain the same advantage even if the beam expander is arranged between the light source side optical system 2 and the sample OB as shown in, for example, FIG. 27.

Sixth Embodiment

The sixth embodiment will be described with respect to FIGS. 28A and 28B, wherein elements similar to the above-stated embodiments are denoted by the same reference numerals, and the explanation thereof is simplified or omitted.

Figure 28A:
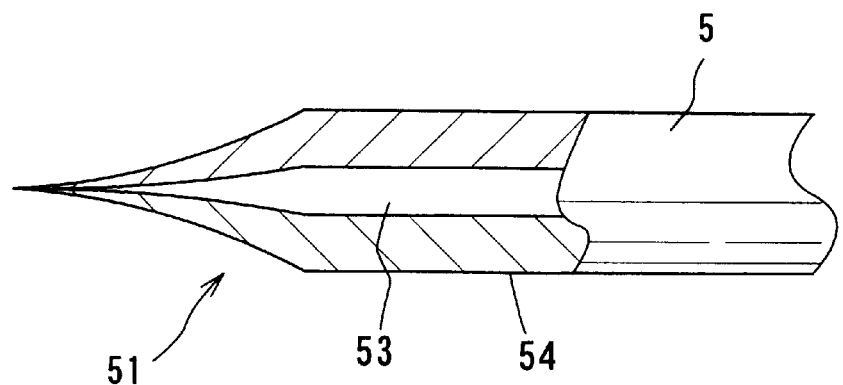
FIGS. 28A and 28B are explanatory views of an optical fiber having a sharpened tip end portion according to the present invention.
Figure 28B:
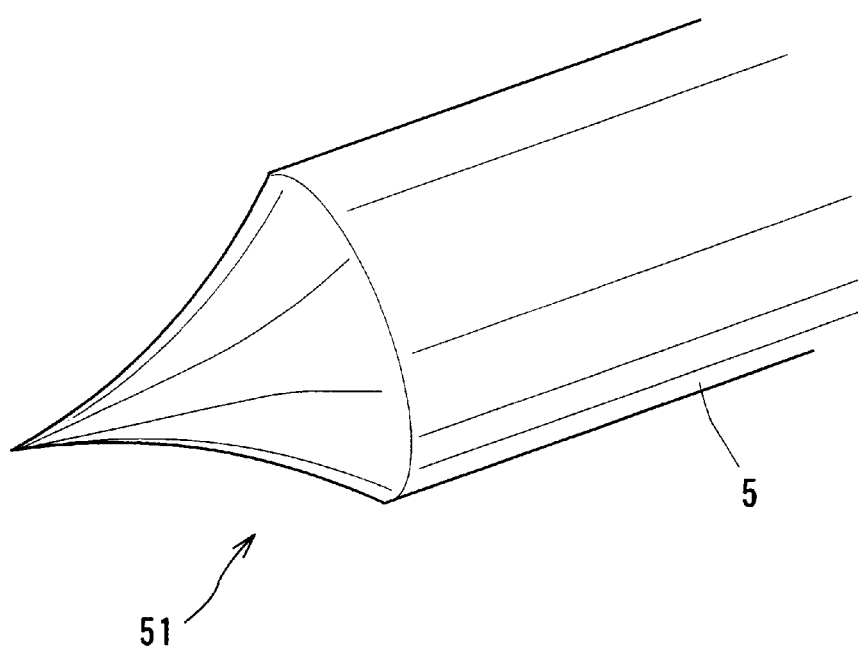

An optical fiber 5 of this embodiment shown in FIGS. 28A and 28B is, for example, the same as that of a scanning probe used for a proximity optical microscope within a scanning probe microscope (SPM), typically a scanning tunnel microscope (STM), which has been recently developed as a microscope exceeding the limit of the light diffraction.

That is, in FIGS. 28A and 28B, this optical fiber 5 has a core 53 and clad 54 at an inner and outer portions thereof, respectively, and a sharpened tip end portion at the target side 51 thereof taking the laser beam via the target to be measured. This sharpened Up end portion of the fiber 5 is sharpened directed toward the target and, for example, formed into corn-like shape shown in FIGS. 28A and 28B. The sharpened tip end portion is made by using a manufacturing method such as a melting and expanding method in which heat is partly applied to the fiber to soften it and the fiber is pulled from the both sides thereof shown in FIGS. 28A and 28B.

Accordingly, if the optical fiber 5 having the sharpened tip end portion is used, the size of the aperture can be further made smaller than that of the original size and spatial resolution for birefringence measurement can be advantageously improved further.

Seventh Embodiment

The seventh embodiment will be described with respect to FIG. 29, wherein elements similar to the above-stated embodiments are denoted by the same reference numerals, and the explanation thereof is simplified or omitted.

Figure 29:
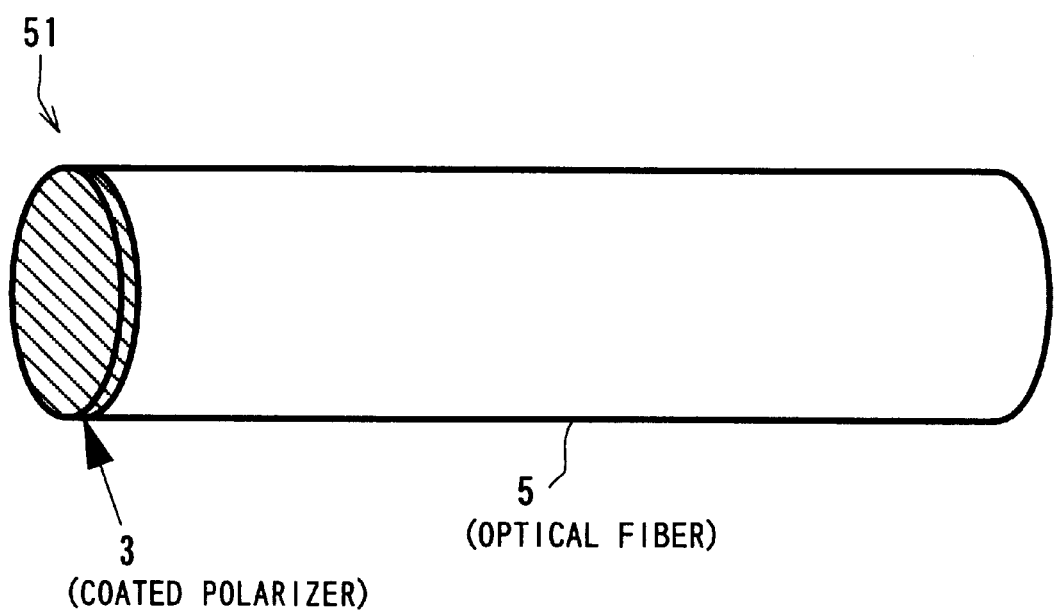
FIG. 29 is an explanatory view of an optical fiber having a detection side optical system integrally bonded thereto according to the present invention.

An optical fiber 5 of this embodiment shown in FIG. 29 is constituted such that a high molecular thin film such as a polarizer or a phase plate, a coated film (including a multilayer film (composite film) of a phase plate and a polarizer) or a detection side optical system 3 comprised of an optical element manufactured by, for example, a coloring processing method after deposition is integrally bonded to the aperture portion using a deposition, sputtering method or the like.

In this embodiment, since the optical fiber and the detection side optical system (polarization element) are integral with each other, the optical fiber can be arranged at a position adjacent a sample with a relatively simple constitution without the need to use a special optical fiber having a photoelastic constant close to zero, and the same advantages as those of the third embodiment can be obtained.

If it is necessary to rotate the polarizer or the like of the detection side optical system based on the birefringence principle, a constitution of rotating the optical fiber itself about the optical axis may be added to the system.

In this embodiment, the detection side optical system is integrally attached to the optical fiber. It is also possible to integrally attach a light source side optical system thereto in case of the optical system shown in, for example, FIG. 23.

Eighth Embodiment

The eighth embodiment will be described with respect to FIG. 30, wherein elements similar to the above-stated embodiments are denoted by the same reference numerals, and the explanation thereof is simplified or omitted.

Figure 30:
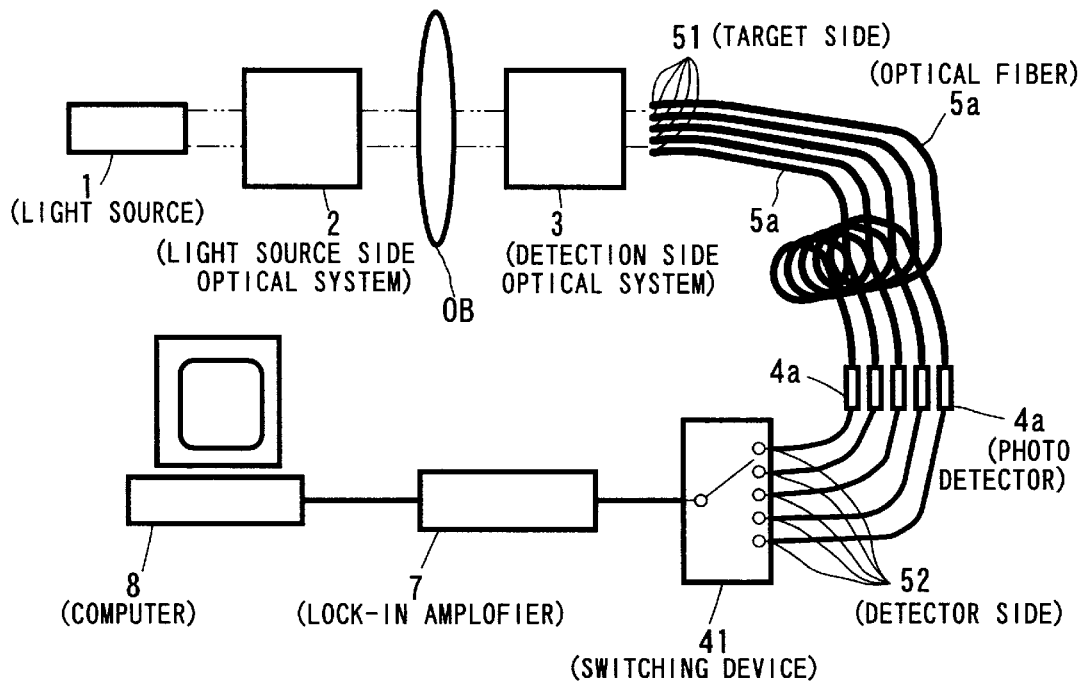
FIG. 30 is a conceptual view of a high spatial resolution polarimetric apparatus if a plurality of optical fibers is used according to the present invention.

In a polarimetric apparatus shown in FIG. 30, a plurality of optical fibers 5a are arranged in parallel on the emission side of a detection side optical system 3 and photo detectors 4a are allotted to the emission sides of the optical fibers 5a, respectively, a photoelectric signal is processed by a lock-in amplifier 7 or a signal processing unit which is not shown such as an A/D converter while switching photoelectric signals detected by the plural photo detectors 4a with a switching device 41.

Figure 31:
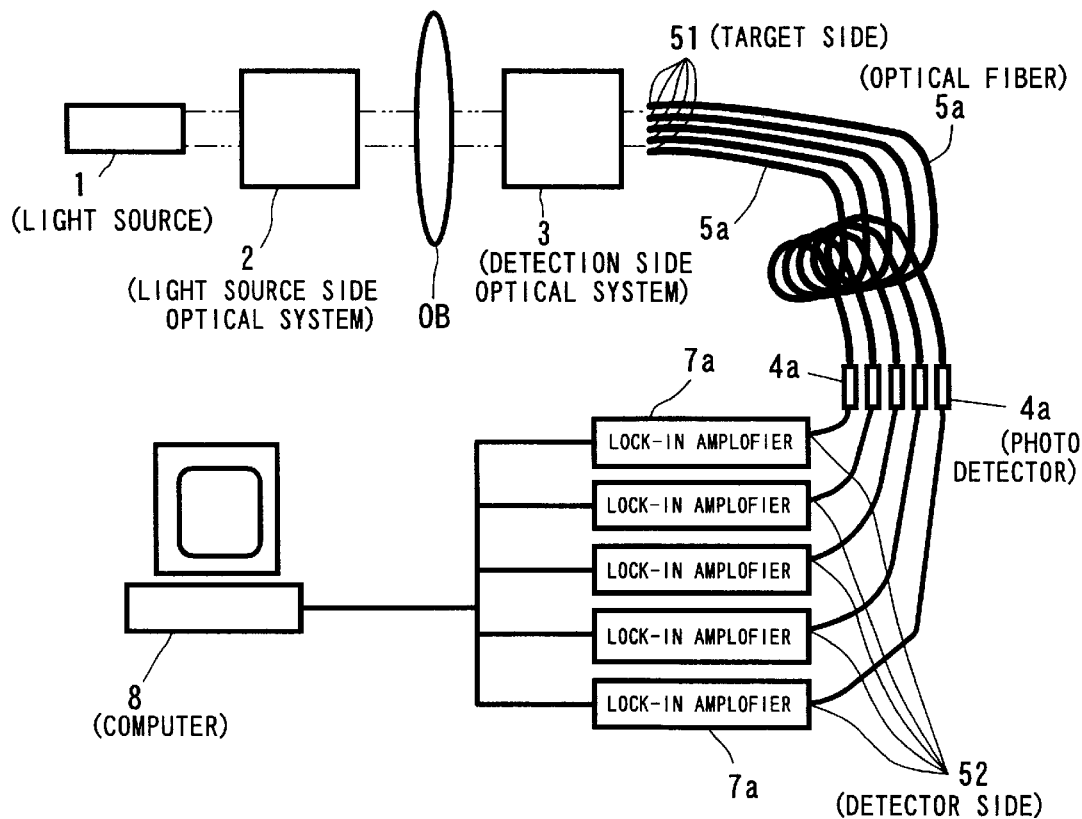
FIG. 31 is a conceptual view of another high spatial resolution polarimetric apparatus if a plurality of optical fibers is used according to the present invention.
Figure 33:
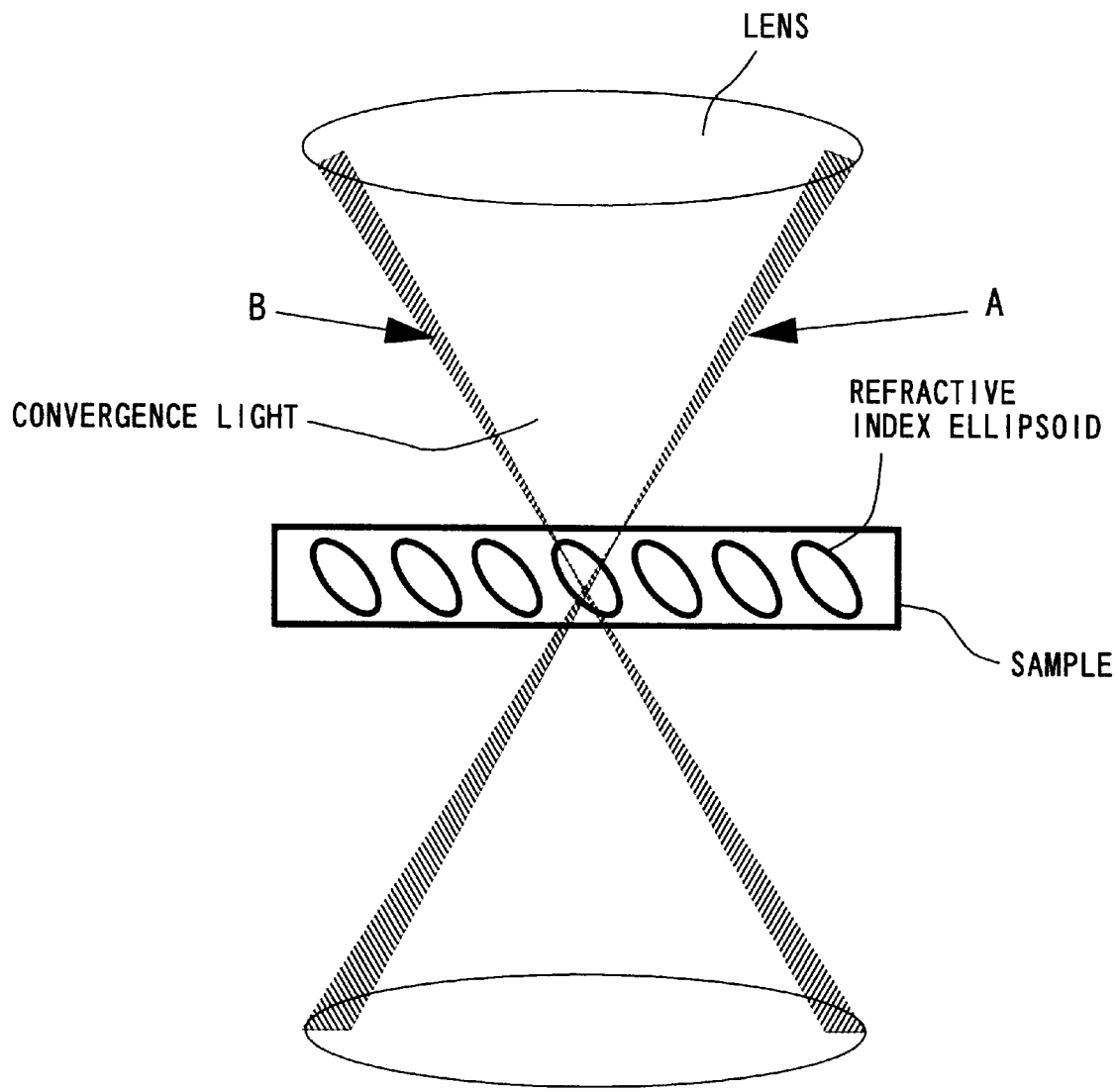
FIG. 33 is a conceptual view for describing a conventional system where a convergent light is incident on a sample.

In this embodiment, the apparatus has a constitution in which channels are switched by the switching device. The present invention should not be limited thereto and may be constituted such that a plurality of lock-in amplifiers 7a are individually connected to the respective photo detectors 4a to carry out parallel processing as shown in, for example, FIG. 31.

The aperture diameter of the optical fibers may not be always the same. If optical fibers having, for example, different aperture diameters are used, it is possible to advantageously measure birefringence with a plurality of spatial resolutions simultaneously. The optical fibers can be arranged either one-dimensionally or two-dimensionally.

The constitutions of the first to eighth embodiments described above may not be always independently provided and they may be appropriately combined within the scope of the present invention.

As stated so far, according to the present invention, the birefringence of a sample or the in-plane distribution characteristics thereof can be quantitatively measured instead of the conventional qualitative observation using a polarization microscope. Compared with, in particular, a conventional case where converged lights are transmitted by a sample using a lens and all of the transmitted lights are detected, parallel lights are transmitted as they are or only the portions which can be regarded as parallel lights can be selectively taken out through a light transmission path represented by an optical fiber. Due to this, the present invention has advantages in that the influence of obliquely incident birefringence on the sample can be prevented and the amount of birefringence can be measured more precisely while enhancing spatial resolution.

Hence, the optical systems and apparatuses according to the present invention allow the observation of the state of a birefringence distribution in the vicinity of the pit of an optical disk, the state of the operation of a liquid crystal display device per pixel, the state of a light waveguide path formed on an optical crystal and the like, and the present invention can be widely applied to the research and development, quality evaluation and maintenance thereof.

What is claimed is:

1. A birefringence measurement optical system comprising:
   a polarized light emission optical system emitting a light signal in a predetermined polarization state toward a target to be measured;
   a polarized light detection optical system detecting the light signal from the polarized light emission optical system through the target, the light signal including birefringence information on the target which can be polarimetrically analyzed;
   a photo detector converting the light signal from the polarized light detection optical system into an electric signal and detecting the electric signal; and
   a light transmission path arranged between the target and the photo detector, the light transmission path taking part of light fluxes of the light signal along an axial direction of the light signal from the target at a target side thereof and transmitting the part of light fluxes from the target side toward a photo detector side thereof, the photo detector receiving the part of light fluxes including the birefringence information, which is higher in spatial resolution than all of the light fluxes, for the birefringence measurement of the target.

2. The birefringence measurement optical system according to claim 1, wherein the light transmission path is an optical fiber having an aperture taking the part of light fluxes at the target side.

3. The birefringence measurement optical system according to claim 2, wherein the optical fiber is arranged between the polarized light detection optical system and the photo detector.

4. The birefringence measurement optical system according to claim 2, wherein the optical fiber has a core constituted by material having a predetermined photoelastic constant.

5. The birefringence measurement optical system according to claim 4, wherein the optical fiber is arranged between the target and the polarized light detection optical system.

6. The birefringence measurement optical system according to claim 2, wherein the optical fiber has a sharpened tip end portion directed toward the target at the target side thereof.

7. The birefringence measurement optical system according to claim 2, wherein the optical fiber is integrally attached to at least part of the polarized light detection optical system.

8. The birefringence measurement optical system according to claim 2, further comprising a mechanism for freely scanning at least a target-side tip end portion of the optical fiber within the light fluxes of the light signal.

9. The birefringence measurement optical system according to claim 2, wherein the optical fiber is a plurality of optical fibers and the plurality of optical fibers are arranged in parallel.

10. A high spatial resolution polarimetric apparatus comprising:
    a birefringence measurement optical system for measuring birefringence information of a target to be measured; and
    analyzing means for analyzing at least one of a retardation, an azimuth angle of a principal axis and an optical rotation angle of the target based on the birefringence Information measured by the birefringence measurement optical system,
    wherein the birefringence measurement optical system includes:
      a polarized light emission optical system emitting a light signal in a predetermined polarization state toward the target;
      a polarized light detection optical system detecting the light signal from the polarized light emission optical system through the target, the light signal including birefringence information on the target which can be polarimetrically analyzed;
      a photo detector converting the light signal from the polarized light detection optical system into an electric signal and detecting the electric signal; and
      a light transmission path arranged between the target and the photo detector, the light transmission path taking part of light fluxes of the light signal along an axial direction of the light signal from the target at a target side thereof and transmitting the part of light fluxes from the target side toward a photo detector side thereof, the photo detector receiving the part of light fluxes including the birefringence information, which is higher in spatial resolution than all of the light fluxes, for the birefringence measurement of the target.

11. The high spatial resolution polarimetric apparatus according to claim 10, wherein the light transmission path is an optical fiber having an aperture taking the part of light fluxes at the target side.

12. The high spatial resolution polarimetric apparatus according to claim 10, wherein the optical fiber is arranged between the polarized light detection optical system and the photo detector.

13. The high spatial resolution polarimetric apparatus according to claim 10, wherein the optical fiber has a core constituted by material having a predetermined photoelastic constant.

14. The high spatial resolution polarimetric apparatus according to claim 13, wherein the optical fiber is arranged between the target and the polarized light detection optical system.

15. The high spatial resolution polarimetric apparatus according to claim 10, wherein the optical fiber has a sharpened tip end portion directed toward the target at the target side thereof.

16. The high spatial resolution polarimetric apparatus according to claim 10, wherein the optical fiber is integrally attached to at least part of the polarized light detection optical system.

17. The high spatial resolution polarimetric apparatus according to claim 10, further comprising a mechanism for freely scanning at least a target side tip end portion of the optical fiber within the light fluxes of the light signal.

18. The high spatial resolution polarimetric apparatus according to claim 10, wherein the optical fiber is a plurality of optical fibers and the plurality of optical fibers are arranged in parallel.

* * * * *